United States Patent
Holmes et al.

(10) Patent No.: US 8,592,365 B2
(45) Date of Patent: *Nov. 26, 2013

(54) SPACER MOIETY FOR POLY(ETHYLENE GLYCOL) MODIFIED PEPTIDE BASED COMPOUNDS

(75) Inventors: Christopher P. Holmes, Saratoga, CA (US); David Tumelty, Sunnyvale, CA (US); Qun Yin, Palo Alto, CA (US)

(73) Assignee: Affymax, Inc., Palo Alto, CA (US)

( * ) Notice: Subject to any disclaimer, the term of this patent is extended or adjusted under 35 U.S.C. 154(b) by 36 days.

This patent is subject to a terminal disclaimer.

(21) Appl. No.: 13/079,615

(22) Filed: Apr. 4, 2011

(65) Prior Publication Data

US 2012/0115796 A1    May 10, 2012

Related U.S. Application Data

(63) Continuation of application No. 10/555,860, filed as application No. PCT/US2004/014887 on May 12, 2004, now Pat. No. 7,919,118.

(60) Provisional application No. 60/469,996, filed on May 12, 2003.

(51) Int. Cl.
*A61K 38/00* (2006.01)

(52) U.S. Cl.
USPC ............................. 514/1.1; 530/300

(58) Field of Classification Search
None
See application file for complete search history.

(56) References Cited

U.S. PATENT DOCUMENTS

| 4,179,337 | A |  | 12/1979 | Davis et al. |
|---|---|---|---|---|
| 4,677,195 | A |  | 6/1987 | Hewick et al. |
| 5,006,333 | A |  | 4/1991 | Saifer et al. |
| 5,278,065 | A |  | 1/1994 | D'Andrea et al. |
| 5,283,317 | A |  | 2/1994 | Saifer et al. |
| 5,292,654 | A |  | 3/1994 | Yoshimura et al. |
| 5,378,808 | A |  | 1/1995 | D'Andrea et al. |
| 5,441,868 | A |  | 8/1995 | Lin |
| 5,468,478 | A |  | 11/1995 | Saifer et al. |
| 5,547,933 | A |  | 8/1996 | Lin |
| 5,580,853 | A |  | 12/1996 | Sytkowski |
| 5,614,184 | A |  | 3/1997 | Sytkowski et al. |
| 5,618,698 | A |  | 4/1997 | Lin |
| 5,621,080 | A |  | 4/1997 | Lin |
| 5,654,276 | A |  | 8/1997 | Barrett et al. |
| 5,668,110 | A |  | 9/1997 | Barrett et al. |
| 5,672,662 | A |  | 9/1997 | Harris et al. |
| 5,677,280 | A |  | 10/1997 | Barrett et al. |
| 5,683,983 | A |  | 11/1997 | Barrett et al. |
| 5,747,446 | A |  | 5/1998 | Sytkowski |
| 5,756,349 | A |  | 5/1998 | Lin |
| 5,767,078 | A |  | 6/1998 | Johnson et al. |
| 5,773,569 | A |  | 6/1998 | Wrighton et al. |
| 5,830,851 | A |  | 11/1998 | Wrighton et al. |
| 5,869,451 | A |  | 2/1999 | Dower et al. |
| 5,891,418 | A | * | 4/1999 | Sharma ........................ 424/1.69 |
| 5,919,758 | A |  | 7/1999 | Sytkowski |
| 5,932,546 | A |  | 8/1999 | Barrett et al. |
| 5,955,422 | A |  | 9/1999 | Lin |
| 5,986,047 | A |  | 11/1999 | Wrighton et al. |
| 6,048,971 | A |  | 4/2000 | Sytkowski et al. |
| 6,077,939 | A |  | 6/2000 | Wei et al. |
| 6,083,913 | A |  | 7/2000 | Dower et al. |
| 6,103,879 | A |  | 8/2000 | Chaovapong et al. |
| 6,107,272 | A |  | 8/2000 | Sytkowski |
| 6,113,906 | A |  | 9/2000 | Greenwald et al. |
| 6,121,238 | A |  | 9/2000 | Dower et al. |
| 6,153,407 | A |  | 11/2000 | Sytkowski et al. |
| 6,211,608 | B1 |  | 4/2001 | Raina et al. |
| 6,221,608 | B1 |  | 4/2001 | Middleton et al. |
| 6,251,864 | B1 |  | 6/2001 | Dower et al. |
| 6,333,031 | B1 |  | 12/2001 | Olsson et al. |
| 6,340,742 | B1 |  | 1/2002 | Burg et al. |
| 6,465,430 | B1 |  | 10/2002 | Dower et al. |
| 6,489,293 | B1 |  | 12/2002 | Sytkowski et al. |
| 6,498,155 | B1 |  | 12/2002 | Luengo et al. |
| 6,506,362 | B1 |  | 1/2003 | Dower et al. |
| 6,531,121 | B2 |  | 3/2003 | Brines et al. |
| 6,552,008 | B1 |  | 4/2003 | Duffy et al. |
| 6,552,167 | B1 |  | 4/2003 | Rose |
| 6,576,235 | B1 |  | 6/2003 | Williams et al. |
| 6,583,272 | B1 |  | 6/2003 | Bailon |
| 6,660,843 | B1 |  | 12/2003 | Feige et al. |

(Continued)

FOREIGN PATENT DOCUMENTS

| EP | 0 400 472 | 12/1990 |
|---|---|---|
| WO | WO 90/12874 | 11/1990 |

(Continued)

OTHER PUBLICATIONS

Abuchowski, A.,et al., "Effect of covalent attachment of polyethylene glycol on immunogenicity and circulating life of bovine liver catalase," J. Biol. Chem, vol. 252, pp. 3582-3586 (1977).

Beauchamp, C.O., et al., "A new procedure for the synthesis of polytheylene glycol-protein adducts; effects on function, receptor recognition, and clearance of superoxide dismutase, lactoferrin, and alpha 2-macroglobulin", Anal Biochem., vol. 131, pp. 25-33 (1983).

Chen, R.H., et al., "Properties of two urate oxidases modified by the covalent attachment of poly(ethylene glycol)", Biochem. Biophys. Acta., vol. 660, pp. 293-298 (1981).

(Continued)

*Primary Examiner* — Thomas Heard
(74) *Attorney, Agent, or Firm* — Fish & Richardson P.C.

(57) ABSTRACT

The present invention relates to a compound comprising a peptide moiety, a spacer moiety and a water-soluble polymer moiety such as a poly(ethylene glycol) moiety. The spacer moiety is between the peptide moiety and the water-soluble polymer moiety. The spacer moiety has the structure:

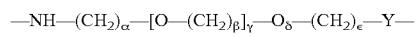

wherein $\alpha$, $\beta$, $\gamma$, $\delta$, and $\epsilon$ are each integers whose values are independently selected.

10 Claims, 24 Drawing Sheets

(56) References Cited

U.S. PATENT DOCUMENTS

| | | | |
|---|---|---|---|
| 6,783,965 | B1 | 8/2004 | Sherman et al. |
| 6,784,154 | B2 | 8/2004 | Westenfelder |
| 6,858,630 | B2 | 2/2005 | Luengo et al. |
| 2002/0015691 | A1 | 2/2002 | Greenwald et al. |
| 2002/0037841 | A1 | 3/2002 | Papadimitriou et al. |
| 2002/0052317 | A1 | 5/2002 | Itri et al. |
| 2002/0115833 | A1 | 8/2002 | Burg et al. |
| 2002/0160013 | A1 | 10/2002 | Olsson et al. |
| 2002/0169128 | A1 | 11/2002 | Sigounas et al. |
| 2002/0177166 | A1 | 11/2002 | Guthridge et al. |
| 2003/0009018 | A1 | 1/2003 | Maeda et al. |
| 2003/0012777 | A1 | 1/2003 | Sherman et al. |
| 2003/0050269 | A1 | 3/2003 | Escary |
| 2003/0104988 | A1 | 6/2003 | Brines et al. |
| 2003/0120045 | A1 | 6/2003 | Bailon |
| 2003/0125262 | A1 | 7/2003 | Kiessling et al. |
| 2003/0134798 | A1 | 7/2003 | Brines et al. |
| 2003/0166249 | A1 | 9/2003 | Williams et al. |
| 2003/0191291 | A1 | 10/2003 | Kochendoerfer et al. |
| 2004/0062746 | A1 | 4/2004 | Martinez et al. |
| 2004/0126361 | A1 | 7/2004 | Saifer et al. |
| 2004/0136952 | A1 | 7/2004 | Bhaskaran et al. |
| 2005/0014240 | A1 | 1/2005 | Sherman et al. |
| 2005/0176627 | A1 | 8/2005 | Cerami et al. |

FOREIGN PATENT DOCUMENTS

| | | | |
|---|---|---|---|
| WO | WO 92/16221 | | 10/1992 |
| WO | WO-92/16555 | | 10/1992 |
| WO | WO-96/40189 | | 12/1996 |
| WO | WO 96/40749 | | 12/1996 |
| WO | WO-96/40750 | | 12/1996 |
| WO | WO-96/40772 | | 12/1996 |
| WO | WO-98/25965 | | 6/1998 |
| WO | WO 00/07629 | | 2/2000 |
| WO | WO 00/12587 | | 3/2000 |
| WO | WO-00/24770 | | 5/2000 |
| WO | WO-00/24782 | | 5/2000 |
| WO | WO-00/33881 | | 6/2000 |
| WO | WO 00/40203 | * | 7/2000 |
| WO | WO 01/38342 | | 5/2001 |
| WO | WO 01/59078 | | 8/2001 |
| WO | WO 01/91780 | | 12/2001 |
| WO | WO-02/065988 | | 8/2002 |
| WO | WO 03/002716 | | 1/2003 |
| WO | WO-2004/014424 | | 2/2004 |
| WO | WO 2004/030617 | | 4/2004 |
| WO | WO 2004/060299 | | 7/2004 |
| WO | WO 2004/060300 | | 7/2004 |
| WO | WO 2004/100997 | | 11/2004 |
| WO | WO-2004/101600 | | 11/2004 |
| WO | WO-2004/101606 | | 11/2004 |
| WO | WO-2004/101611 | | 11/2004 |
| WO | WO-2004/108070 | | 12/2004 |

OTHER PUBLICATIONS

Dubowchik et al.: "Doxorubicin Immunoconjugates Containing Bivalent Lysosomally-Cleavable Dipeptide Linkages" Bioorganic & Medicinal Chemistry Letters 12 (2002) pp. 1529-1532.

Ei-Sayed et al., "Extravasation of poly(amidoamine) (PAMAM) dendrimers across microvascular network endothelium", Pharm. Res., 2001, 18:23-28.

Francis, G.E., et al., "PEGylation of cytokines and other therapeutic proteins and peptides: The importance of biological optimisation of coupling techniques", Int. J. Hematol, vol. 68, pp. 1-18 (1998).

Gestwicki et al., "Influencing receptor-ligand binding mechanisms with multivalent ligand architecture", J. Amer. Chem. Soc., 2002, 124:14922-14933.

Greenwald et al., "Controlled release of proteins from their poly(ethylene glycol) conjugates: Drg delivery systems employing 1,6-elimination." Bioconjugate Chemistry. vol. 14, No. 2, pp. 395-403 (Apr. 3, 2003).

Greenwald et al., "Effective drug delivery by PEGylated drug conjugates", Advanced Drug Delivery Reviews. Amsterdam, NL. vol. 55, N. 2, pp. 217-250 (Feb. 10, 2003).

Johnson et al., "Identification of a 13 amino acid peptide mimetic of erythropoietin and description of amino acids critical for the mimetic activity of EMP1", Biochemistry 37: 3699-3710 (1998).

Johnson, D.L., et al., "Amino-terminal dimerization of an erythropoietin mimetic peptide results in increased erythropoietic activity", Chem. Biol., vol. 4, pp. 939-950 (1997).

Kita, Y., et al., "Characterization of a polyethylene glycol conjugate of recombinant human interferon-gamma", Dr. Des. Deliv. vol. 6, pp. 157-167 (1990).

Klajnert et al., "Dendrimers: properties and applications", Acta Biochimica Polonica, 2001, 48:199-208.

Knauf, M.J., et al., "Relationship of effective molecular size to systemic clearance in rats of recombinant interleukin-2 chemically modified with water-soluble polymers", J. Biol. Chem., vol. 263, pp. 15064-15070 (1988).

Lee, J.W., et al., "Reduction of azides to primary amines in substrates bearing labile ester functionality. Synthesis of a PEG-solubilized, "Y"-shaped iminodiacetic acid reagent for preparation of folate-tethered drugs", Org. Lett., vol. 1, pp. 179-181 (1999).

Ramakrishnan et al., "Pharmacokinetic and pharmacodynamic modeling of recombinant human erythropoeitin after single and multiple doses in healthy volunteers", J. Clin. Pharmacol., 2004, 44:991-992.

Saifer, M.G., et al., "Plasma clearance and immunologic properties of long-acting superoxide dismutase prepared using 35,000 to 120,000 dalton poly-ethylene glycol", Adv. Exp. Med. Biol. vol. 366, pp. 377-387 (1994).

Sasaki, et al., "Carbohydrate structure of erythropoietin expressed in Chinese hamster ovary cells by a human erythropoietin cDNA", Journal of Biological Chemistry 262:12059-12076 (1987).

Somack, R., et al., "Preparation of long-acting superoxide dismutase using high molecular weight polyethylene glycol (41,000-72,000 daltons)", Free. Radic. Res. Commun. vols. 12-13, pp. 553-562 (1991).

Tsutsumi, Y. et al., "Polyethylene glycol modification of interleukin-6 enhances its thrombopoietic activity", J. Controlled Release, vol. 33, pp. 447 (1995).

Veronese, F. M., "Peptide and protein PEGylation: a review of problems and solutions", Biomaterials 22:405-417 (2001).

Woller, N.C. et al., "The lectin-binding propertiesof six generations of mannose-functionaled dendrimers", Organic Letters 4:7-10 (2002).

Wrighton et al., "Increased Potency of an Erithropoietin Peptide Mimetic Through Covalent Dimerization." Nature Biotechnology, Nature Publishing, US, vol. 15, (Nov. 1, 1997).

Wrighton et al., "Small peptides as potent mimetics of the protein hormone erythropoietin", Science 273:458-463 (1996).

* cited by examiner

Synthesis of H-TAP-Boc molecule
Synthesis of Cbz-TAP

Synthesis of Cbz-TAP-Boc

Synthesis of Boc-TAP

PEGylation of Peptide, with mPEG-NPC

Peptide with TAP on C-terminus:

mPEG-NPC

PEGylation of Peptide, with mPEG-SPA

Peptide with TAP on C-terminus:

mPEG-SPA

Synthesis of Peptide Dimer with Spacer, Attached to Resin
Synthesis of TentaGel-Linker:

(TentaGel bromide)      (TentaGel-linker)

Synthesis of TentaGel-Linker-TAP(Boc)

(TentaGel-Linker)      (TentaGel-Linker-TAP(Boc))

Synthesis of TentaGel-Linker-TAP-Lys (TentaGel-Linker-TAP(Boc))      (TentaGel-Linker-TAP-Lys)

PEGylation of Peptide Dimer with Spacer, with mPEG-NPC mPEG-NPC

Ion Exchange Purification m=1-5, n = 1-14, m and n are integers m=1-5, n = 1-14, m and n are integers m=1-5, n = 1-14, m and n are integers m=1-5, n = 1-14, m and n are integers Synthesis of Homotrifunctional Molecules
Branched homotrifunctional molecules having the structure m=1-2, n = 1-6, m and n are integers m = 1-2, n = 1-6, m and n are integers C-Terminus Dimerization and PEGylation Using A Trifunctional Molecule
A trifunctional molecule having the structure N-Terminus Dimerization and PEGylation Using A Trifunctional Molecule A trifunctional molecule having the structure

SPACER MOIETY FOR POLY(ETHYLENE GLYCOL) MODIFIED PEPTIDE BASED COMPOUNDS

CROSS-REFERENCE TO RELATED APPLICATIONS

This application is a continuation of U.S. patent application Ser. No. 10/555,860, filed Nov. 1, 2005 now U.S. Pat. No. 7,919,118, which in turn claims the benefit of International Application No. PCT/US2004/014887, filed May 12, 2004, which in turn claims the benefit of U.S. Provisional Application No. 60/469,996, filed on May 12, 2003, each of which are incorporated herein by reference in their entirety.

FIELD OF THE INVENTION

The present invention relates to a novel method for covalently attaching a water soluble polymer, for example poly(ethylene glycol) (PEG) to peptides and peptide-based compounds. In addition, the invention relates to novel therapeutic compositions comprising such compounds.

BACKGROUND OF THE INVENTION

In recent years, with the development of research on proteins, a great number of peptides having various actions have been found. With the progress of genetic recombination techniques and organic synthetic methods of peptides, it has become possible to obtain these physiologically active peptides and their structurally analogous compounds in a large amount. Many of these peptides having special activity are extremely useful as pharmaceuticals.

Examples of such peptides include peptides that bind to erythropoietin (EPO) receptors (EPO-R). EPO is a glycoprotein hormone with 165 amino acids, 4 glycosylation sites on amino acid positions 24, 38, 83, and 126, and a molecular weight of about 34,000. It stimulates mitotic division and the differentiation of erythrocyte precursor cells and thus ensures the production of erythrocytes. EPO is essential in the process of red blood cell formation, the hormone has potentially useful applications in both the diagnosis and the treatment of blood disorders characterized by low or defective red blood cell production. A number of peptides that interact with the EPO-R have been discovered. (See e.g., U.S. Pat. No. 5,773,569 to Wrighton et al.; and U.S. Pat. No. 5,830,851 to Wrighton et al.; WO 01/91780 to Smith-Swintosky et al.)

However, the clearance of peptides, particularly when administered in the circulatory system, is generally very fast. Therefore, it is desirable to improve the durability of such peptides. In addition, when the peptides are obtained from different species of animals, designed by peptide protein engineering, and/or having structures different from those of the subject, there is a risk of causing serious symptoms due to the production of antibodies. Hence, it is also desirable to improve the antigenicity of such peptides. In order to use these peptides as pharmaceuticals, it is necessary to have both improved antigenicity and durability.

Chemical modification of the peptides with macromolecular compounds such as poly(ethylene glycol) has been shown to be effective to improve the antigenicity and durability of various peptides. Thus, poly(ethylene glycol) and poly(ethylene glycol) derivatives have been widely used as peptide-modifying macromolecular reagents.

In its most common form, poly(ethylene glycol) has the following structure:

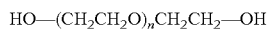

The above polymer, alpha-, omega-dihydroxyl poly(ethylene glycol) can be represented in brief form as HO-PEG-OH where it is understood that the -PEG- symbol represents the following structural unit:

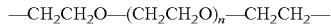

Without being limited to any particular theory or mechanism of action, the long, chain-like PEG molecule or moiety is believed to be heavily hydrated and in rapid motion when in an aqueous medium. This rapid motion is believed to cause the PEG to sweep out a large volume and prevents the approach and interference of other molecules. As a result, when attached to another chemical entity (such as a peptide), PEG polymer chains can protect such chemical entity from immune response and other clearance mechanisms. As a result, PEGylation leads improved drug efficacy and safety by optimizing pharmacokinetics, increasing bioavailability, and decreasing immunogenicity and dosing frequency.

For example, some active derivatives of PEG have been attached to peptides, proteins and enzymes with beneficial results. PEG is soluble in organic solvents. PEG attached to enzymes can result in PEG-enzyme conjugates that are soluble and active in organic solvents. Attachment of PEG to protein can reduce the immunogenicity and rate of kidney clearance of the PEG-protein conjugate as compared to the unmodified protein, which may result in dramatically increased blood circulation lifetimes for the conjugate.

For example, covalent attachment of PEG to therapeutic proteins such as interleukins (Knauf, M. J. et al., J. Biol. Chem. 1988, 263, 15,064; Tsutsumi, Y. et al., J. Controlled Release 1995, 33, 447), interferons (Kita, Y. et al., Drug Des. Delivery 1990, 6, 157), catalase (Abuchowski, A. et al., J. Biol. Chem. 1977, 252, 3, 582), superoxide dismutase (Beauchamp, C. O. et al., Anal. Biochem. 1983, 131, 25), and adenosine deaminase (Chen, R. et al., Biochim. Biophy. Acta 1981, 660, 293), has been reported to extend their half life in vivo, and/or reduce their immunogenicity and antigenicity.

In addition, PEG attached to surfaces can reduce protein and cell adsorption to the surface and alter the electrical properties of the surface. Similarly, PEG attached to liposomes can result in a great increase in the blood circulation lifetime of these particles and thereby possibly increase their utility for drug delivery. (J. M. Harris, Ed., "Biomedical and Biotechnical Applications of Polyethylene Glycol Chemistry," Plenum, New York, 1992).

The presence of an amino acid or peptide arm between PEG and the attached macromolecule has demonstrated several advantages due to the variability of properties that may be introduced using a suitable amino acid or peptide. Of these amino acid or peptide arms, Norleucine (Nle) is used for analytical purposes; $^{14}$C or tritium labeled Gly is used for pharmacokinetic studies; Lys is used for branching; and Met-Nle or Met-βAla is used for PEG removal by BrCN treatment (Veronese, F. M. Biomaterials, 2001, 22, 405).

Another known type of PEG derivative with amino acid arm between PEG and the attached macromolecules is characterized by two linear PEG chains linked together through two functions of a tri-functional spacer while the third function is used to bind the protein. Lysine is the tri-functional amino acid spacer and the two PEG chains are linked to its alpha and epsilon amino groups while the carboxylic group is activated as hydroxysuccinimidyl esters for protein binding. This PEG derivative has the advantage of a lower inactivation of the enzymes during conjugation and its "umbrella-like" structure is effective in protecting proteins from proteolysis, in the approach of antibodies and in reducing immunogenicity (Veronese, F. M. Biomaterials, 2001, 22, 405).

PEG-linker-peptide or PEG-linker-liposome are sometimes formed as undesirable by-products when part of the activating group was incorporated into the final PEG-peptide or PEG-liposome adduct. Frances et al. (Int. J. Hematol. 1998, 68, 1) disclose that such linkers can have several types of adverse effects: (1) these linkers are not necessarily immunologically inert and there is experimental evidence that such groups are responsible for immunogenicity/antigenicity of PEG proteins; (2) some linkers moieties contain labile bonds that can be cleaved enzymatically or chemically; (3) linker moieties derived from often relatively toxic activated PEGs could lead to regulatory problems; (4) certain linker group such as triazine ring could cause crosslinking.

Despite the advances made in the area of the PEG-modified peptide-based compounds, there remains a need for novel PEG-modified compounds with improved antigenicity and durability.

The citation and/or discussion of a reference in this section, and throughout this specification, shall not be construed as an admission that such reference is prior art to the present invention.

SUMMARY OF THE INVENTION

The present invention relates to a peptide-based compound comprising a peptide moiety, a spacer moiety, and a water-soluble polymer moiety such as poly(ethylene glycol). The spacer moiety is between the peptide and the water-soluble polymer moiety.

The present invention also relates to a peptide-based compound that further comprises a linker moiety. The spacer moiety is between the linker moiety and the water-soluble polymer moiety and the linker moiety is between the spacer moiety and the peptide. Alternatively, the linker moiety may comprise the spacer moiety.

In one embodiment of the present invention, the spacer moiety has the following structure:

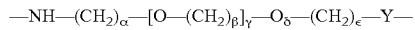

wherein $\alpha$, $\beta$, $\gamma$, $\delta$, and $\epsilon$ are each integers whose values are independently selected.

In preferred embodiments,
$\alpha$ is an integer, $1 \leq \alpha \leq 6$;
$\beta$ is an integer, $1 \leq \beta \leq 6$;
$\epsilon$ is an integer, $1 \leq \epsilon \leq 6$;
$\delta$ is 0 or 1;
$\gamma$ is an integer, $0 \leq \gamma \leq 10$; and
Y is either NH or CO.
In certain preferred embodiments, $\beta=2$ when $\gamma>1$.
In one particularly preferred embodiment,
$\alpha=\beta=\epsilon=2$;
$\gamma=\delta=1$; and
Y is NH.
In other embodiments,
$\gamma=\delta=0$;
$2 \leq \alpha+\epsilon \leq 5$; and
Y is CO.
In certain other embodiments,
$\gamma=\delta=0$;
$\alpha+\epsilon=5$; and
Y is CO.
In other embodiments
$\alpha=2$;
$\gamma=\delta=\beta=\epsilon=0$; and
Y is CO.

In one embodiment of the present invention, the linker moiety has the following structure:

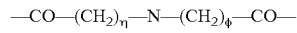

wherein $\eta$ and $\phi$ are each integers whose values are independently selected and N may be covalently bonded to Y of the spacer moiety.

In preferred embodiments,
$\eta$ is an integer, $1 \leq \eta \leq 6$; and
$\phi$ is an integer, $1 \leq \phi \leq 6$.
In one particularly preferred embodiment,
$\eta=\phi=1$.

In another embodiment the linker moiety is a lysine residue or a lysine amide (a lysine residue wherein the carboxyl group has been converted to an amid moiety-$CONH_2$).

Preferably, the water-soluble polymer moiety is a poly(ethylene glycol) moiety. More preferably the poly(ethylene glycol) moiety is linear and has a molecular weight of more than 10 KDaltons. Even more preferably the poly(ethylene glycol) moiety has a molecular weight of from about 20 to 60 KDaltons. Most preferably the poly(ethylene glycol) moiety has a molecular weight of 20 KDaltons. Preferably, the poly(ethylene glycol) moiety has a polydispersity value ($M_w/M_n$) of less than 1.20, more preferably less than 1.1, and most preferably less than 1.05. The water-soluble polymer moiety may be dimeric and comprise two monomeric water-soluble polymers linked by a linker or spacer moiety.

In one embodiment on the invention, the peptide moiety is dimeric and comprises two monomeric peptides and linked by a linker moiety.

In one embodiment, the peptide moiety is selected from peptides which bind to erythropoietin-receptors. Non-limiting examples of such EPO-R binding peptides include those disclosed in published international applications PCT/US00/32224 (publication no. WO 01/38342 A2, U.S. designated), PCT/US96/09810 (publication no. WO 96/40749, U.S. designated) and PCT/US01/16654 (publication no. WO 01/91780 A1); and U.S. Pat. Nos. 5,767,078, 5,773,569, 5,830,851, 5,986,047 and 6,221,608. Additional non-limiting examples of such EPO-R binding peptides disclosed in U.S. Provisional Application Ser. Nos. 60/470,245; 60/469,993; and 60/470,244, all of which were filed on May 12, 2004.

In another embodiment, the peptide moiety is selected from peptides which bind to thrombopoietin-receptors ("TPO-R"). Non-limiting examples of such TPO-R binding peptides include those disclosed in U.S. Pat. Nos. 6,552,008, 6,506,362, 6,498,155, 6,465,430, 6,333,031, 6,251,864, 6,121,238, 6,083,913, 5,932,546, 5,869,451, 5,683,983, 5,677,280, 5,668,110, and 5,654,276; and published U.S. Patent Applications 2003/0083361, 2003/0009018, 2002/0177166 and 2002/0160013.

The present invention also relates to a pharmaceutical composition comprising the compound(s) described above.

BRIEF DESCRIPTION OF THE DRAWINGS

FIG. 1A illustrates synthesis of Cbz-TAP from TAP; FIG. 1B illustrates synthesis of Cbz-TAP-Boc from Cbz-TAP; and FIG. 1C illustrates s synthesis of H-TAP-Boc from Cbz-TAP-Boc.

FIG. 7A shows synthesis of a "TentaGel-linker" from TentaGel bromide. FIG. 7B shows synthesis of TentaGel-Linker-TAP (Boc) from TentaGel-linker. FIG. 7C shows synthesis of TentaGel-Linker-TAP-Lys from TentaGel-Linker-TAP (Boc). FIG. 7D shows synthesis of TentaGel-Linker-TAP-Lys (Peptide)$_2$ from TentaGel-Linker-TAP-Lys. FIG. 7E shows cleavage of peptide dimer with spacer from resin. FIG. 7F shows oxidation of dimeric peptide to yield dimerized peptide with disulfide bonds.

FIG. 11C illustrates a reaction scheme for synthesis of the trifunctional molecule in FIG. 11A.

FIG. 12C illustrates a reaction scheme for synthesis of the trifunctional molecule in FIG. 12A.

FIG. 13B illustrates a reaction scheme for synthesis of the homotrifunctional molecule illustrated in FIG. 13A.

FIG. 14B illustrates a reaction scheme where the trifunctional molecule is used in C-terminus dimerization and PEGylation of a peptide, the monomer of which is SEQ ID NO:2.

FIG. 15A-15C illustrates a reaction schemes for synthesis of the trifunctional molecule. FIG. 15D illustrates a reaction scheme where the trifunctional molecule is used in N-terminus dimerization and PEGylation of a peptide, the monomer of which is SEQ ID NO:3.

FIG. 16A illustrates the structure of the trifunctional linker used in the reaction schemes. A reaction scheme for coupling of the trifunctional linker to peptide monomers (SEQ ID NO:4) is illustrated in FIG. 16B. FIG. 16C illustrates a reaction scheme where the peptide dimer is PEGylated via a carbamate bond. FIG. 16D shows a reaction scheme where the peptide dimer is PEGylated via an amide bond.

DETAILED DESCRIPTION

Definitions

Figure 1A:
FIGS. 1A-1C show reaction schemes illustrating the synthesis of an H-TAP-Boc molecule.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. The unconventional amino acids in peptides are abbreviated as follows: 1-naphthylalanine is 1-nal or $N_p$; 2-naphthylalanine is 2-nal; N-methylglycine (also known as sarcosine) is MeG or $S_c$; and acetylated glycine (N-acetylglycine) is AcG.

"Peptide" or "polypeptide" refers to a polymer in which the monomers are alpha amino acids joined together through amide bonds. Peptides are two or often more amino acid monomers long. Preferably, peptides of the present invention contain less than about fifty amino acid monomers in length.

As used herein, the phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

As used herein the term "agonist" refers to a biologically active ligand which binds to its complementary biologically active receptor and activates the latter either to cause a biological response in the receptor, or to enhance preexisting biological activity of the receptor.

Spacer Moiety

In the present invention, a peptide moiety is attached to a PEG moiety via a spacer moiety has the following structure:
In one embodiment of the present invention, the spacer moiety has the following structure:

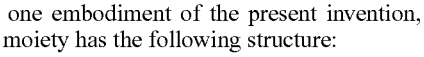

wherein α, β, γ, δ, and ε are each integers whose values are independently selected.

In preferred embodiments,
α is an integer, $1 \leq \alpha \leq 6$;
β is an integer, $1 \leq \beta \leq 6$;
ε is an integer, $1 \leq \varepsilon \leq 6$;
δ is 0 or 1;
γ is an integer, $0 \leq \gamma \leq 10$; and
Y is either NH or CO.

In certain preferred embodiments, $\gamma=2$ when $\gamma>1$.
In one particularly preferred embodiment,
$\alpha=\beta=\epsilon=2$;
$\gamma=\delta=1$; and
Y is NH.
In other embodiments,
$\gamma=\delta=0$;
$2\leq\alpha+\epsilon\leq5$; and
Y is CO.
In certain other embodiments,
$\gamma=\delta=0$;
$\alpha+\epsilon=5$; and
Y is CO.
In other embodiments
$\alpha=2$;
$\gamma=\delta=\beta=\epsilon=0$; and
Y is CO.

According to the invention, a water-soluble polymer moiety (preferably PEG) is attached to the NH terminus of the spacer. The water-soluble moiety may be attached directly to the spacer or it may be attached indirectly, for example with an amide or carbamate linkage(s). In such embodiments, the PEG moiety comprises at least one monomeric PEG chain.

In certain embodiments the PEG moiety comprises two monomeric PEG chains. Preferably the two monomeric PEG chains are linked together through lysine residue or a lysine amide (a lysine residue wherein the carboxyl group has been converted to an amide moiety-$CONH_2$). More preferably, the two PEG chains are linked to lysine's alpha and epsilon amino groups while the carboxylic group is activated as hydroxysuccinimidyl esters for binding to the spacer moiety. For example, when a lysine amide links the two monomeric PEG chains the dimer may be illustrated structurally as shown in Formula I, and summarized as shown in Formula II:

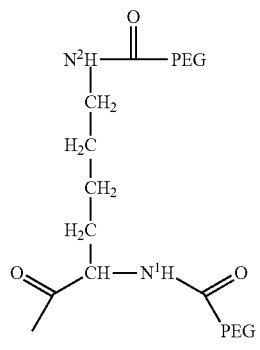

Formula I

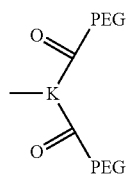

Formula II

In Formula I, $N^2$ represents the nitrogen atom of lysine's $\epsilon$-amino group and $N^1$ represents the nitrogen atom of lysine's $\alpha$-amino group. In preferred embodiments, the C-terminal lysine of the two peptide monomers is L-lysine. In alternative embodiments, one or more lysine residues can be D-lysine.

According to the invention the peptide moiety is attached to the Y terminus of the spacer. The spacer maybe attached to either the C-terminus or the N-terminus of the peptide. Hence, in embodiments where the spacer is attached to the C-terminus of the peptide, Y is NH. In embodiments where the spacer is attached to the N-terminus of the peptide, Y is CO. In alternative preferred embodiments, a spacer of the invention wherein Y is NH is attached by an amide bond with the $\epsilon$-amino group of the C-terminal lysine residue of the peptide monomer.

Linker Moiety

In another preferred embodiment, the spacer of the invention is attached to a peptide as part of a trifunctional linker (described below). In this embodiment, Y of the spacer moiety is CO and Y of the spacer moiety forms an amide bond with an N atom of the trifunctional linker.

In one particular preferred embodiment, the linker moiety is a trifunctional linker having the following structure:

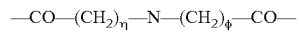

wherein $\eta$ and $\phi$ are each integers whose values are independently selected, N is covalently bonded to Y of the spacer moiety, and Y of the spacer moiety is CO.

In preferred embodiments,
$\eta$ is an integer, $1\leq\eta\leq6$; and
$\phi$ is an integer, $1\leq\phi\leq6$.
In one particularly preferred embodiment,
$\eta=\phi=1$.

The spacer moiety may be incorporated into the peptide during peptide synthesis. For example, where a spacer contains a free amino group and a second functional group (e.g., a carboxyl group or an amino group) that enables binding to another molecular moiety, the spacer may be conjugated to the solid support. Thereafter, the peptide may be synthesized directly onto the spacer's free amino group by standard solid phase techniques.

In a preferred embodiment, a spacer containing two functional groups is first coupled to the solid support via a first functional group. When a dimer peptide is to be synthesized, optionally a linker $L_K$ moiety having two or more functional groups capable of serving as initiation sites for peptide synthesis and an additional functional group (e.g., a carboxyl group or an amino group) that enables binding to another molecular moiety is conjugated to the spacer via the spacer's second functional group and the linker's third functional group. Thereafter, two peptide monomers may be synthesized directly onto the two reactive nitrogen groups of the linker $L_K$ moiety in a variation of the solid phase synthesis technique. For example, a solid support coupled spacer with a free amine group may be reacted with a lysine linker via the linker's free carboxyl group.

In another embodiment, the spacer moiety may be conjugated to the peptide after peptide synthesis. Such conjugation may be achieved by methods well established in the art. In one embodiment, the linker contains at least one functional group suitable for attachment to the target functional group of the synthesized peptide. For example, a spacer with a free amine group may be reacted with a peptide's C-terminal carboxyl group.

Water-Soluble Polymer/PEG Moiety

Water-soluble polymer moiety of the present invention include, but are not limited to, (a) polyalkylene glycol and derivatives thereof, including PEG, mPEG, PEG homopolymers, polypropylene glycol homopolymers, copolymers of ethylene glycol with propylene glycol, wherein said homopolymers and copolymers are unsubstituted or substituted at one end with an alkyl group; (b) cellulose and cellulose derivatives, including methylcellulose and carboxymethyl cellulose; (c) starch and dextrines, and derivatives thereof; (d) dextran and dextran derivatives, including dextran sulfate, cross linked dextrin, and carboxymethyl dextrin; (e) heparin and fragments of heparin; (f) polyvinyl alcohol and polyvinyl ethyl ethers; (g) polyvinylpyrrolidone; (h) a,b-poly[(2-hydroxyethyl)-DL-aspartamide; and (i) polyoxyethylated polyols.

These polymers can be linear, branched, or star-shaped with a wide range of molecular weight.

The water-soluble polymer moiety preferably is PEG. The preferred PEG for use in the present invention is linear PEG having a molecular weight of more than 20 KDaltons. Preferably the PEG has a molecular weight of from about 20 KDaltons to about 60 KDaltons. More preferably the PEG has a molecular weight of from about 20 KDaltons to about 40 KDaltons. Most preferably, the PEG has a molecular weight of about 20 KDaltons.

The water-soluble polymer moiety is covalently attached to the spacer or linker moiety. In one embodiment, a PEG moiety is attached to the N-terminus of the spacer.

The compounds of the present invention may comprise multiple water-soluble polymer moieties (preferably PEG moieties) (e.g., 2, 3, 4, or more), at least one of such multiple water-soluble polymer moieties is linked through a spacer moiety. Where the compound comprises more than one water-soluble polymer moieties, the multiple water-soluble polymer moieties may be the same or different chemical moieties (e.g., PEGs of different molecular weight). In one embodiment of the invention, the water-soluble polymer moiety is dimeric and comprises two monomeric PEGs linked by a spacer moiety. In some cases, the degree of PEGylation (the number of PEG moieties attached to a peptide and/or the total number of peptides to which a PEG is attached) may be influenced by the proportion of PEG molecules versus peptide molecules in a PEGylation reaction, as well as by the total concentration if each in the reaction mixture. In general, the optimum PEG versus peptide ratio (in terms of reaction efficiency to provide for no excess unreacted peptides and/or PEG) will be determined by factors such as the desired degree of PEGylation (e.g., mono, di-, tri-, etc.), the molecular weight of the polymer selected, whether the polymer is branched or unbranched, and the reaction conditions for a particular attachment method.

There are a number of PEG attachment methods available to those skilled in the art [see, e.g., Goodson, et al. (1990) Bio/Technology 8:343 (PEGylation of interleukin-2 at its glycosylation site after site-directed mutagenesis); EP 0 401 384 (coupling PEG to G-CSF); Malik, et al., (1992) Exp. Hematol. 20:1028-1035 (PEGylation of GM-CSF using tresyl chloride); PCT Pub. No. WO 90/12874 (PEGylation of erythropoietin containing a recombinantly introduced cysteine residue using a cysteine-specific mPEG derivative); U.S. Pat. No. 5,757,078 (PEGylation of EPO peptides); U.S. Pat. No. 5,672,662 (Poly(ethylene glycol) and related polymers monosubstituted with propionic or butanoic acids and functional derivatives thereof for biotechnical applications); U.S. Pat. No. 6,077,939 (PEGylation of an N-terminal α-carbon of a peptide); Veronese et al., (1985) Appl. Biochem. Bioechnol 11:141-142 (PEGylation of an N-terminal α-carbon of a peptide with PEG-nitrophenylcarbonate ("PEG-NPC") or PEG-trichlorophenylcarbonate); and Veronese (2001) Biomaterials 22:405-417 (Review article on peptide and protein PEGylation)].

For example, PEG may be covalently bound to amino acid residues via a reactive group. Reactive groups are those to which an activated PEG molecule may be bound (e.g., a free amino or carboxyl group). For example, N-terminal amino acid residues and lysine (K) residues have a free amino group; and C-terminal amino acid residues have a free carboxyl group. Sulfhydryl groups (e.g., as found on cysteine residues) may also be used as a reactive group for attaching PEG. In addition, enzyme-assisted methods for introducing activated groups (e.g., hydrazide, aldehyde, and aromatic-amino groups) specifically at the C-terminus of a polypeptide have been described [Schwarz, et al. (1990) Methods Enzymol. 184:160; Rose, et al. (1991) Bioconjugate Chem. 2:154; Gaertner, et al. (1994) J. Biol. Chem. 269:7224].

For example, PEG molecules may be attached to amino groups using methoxylated PEG ("mPEG") having different reactive moieties. Non-limiting examples of such reactive moieties include succinimidyl succinate (SS), succinimidyl carbonate (SC), mPEG-imidate, para-nitrophenylcarbonate (NPC), succinimidyl propionate (SPA), and cyanuric chloride. Non-limiting examples of such mPEGs include mPEG-succinimidyl succinate (mPEG-SS), mPEG$_2$-succinimidyl succinate (mPEG$_2$-SS); mPEG-succinimidyl carbonate (mPEG-SC), mPEG$_2$-succinimidyl carbonate (mPEG$_2$-SC); mPEG-imidate, mPEG-para-nitrophenylcarbonate (mPEG-NPC), mPEG-imidate; mPEG$_2$-para-nitrophenylcarbonate (mPEG$_2$-NPC); mPEG-succinimidyl propionate (mPEG-SPA); mPEG$_2$-succinimidyl propionate (mPEG$_2$-SPA); mPEG-N-hydroxy-succinimide (mPEG-NHS); mPEG$_2$-N-hydroxy-succinimide (mPEG$_2$-NHS); mPEG-cyanuric chloride; mPEG$_2$-cyanuric chloride; mPEG$_2$-Lysinol-NPC, and mPEG$_2$-Lys-NHS.

Where attachment of the PEG is non-specific and a peptide containing a specific PEG attachment is desired, the desired PEGylated compound may be purified from the mixture of PEGylated compounds. For example, if an N-terminally PEGylated peptide is desired, the N-terminally PEGylated form may be purified from a population of randomly PEGylated peptides (i.e., separating this moiety from other monoPEGylated moieties).

In some embodiments, PEG is attached site-specifically to a peptide or a spacer. Site-specific PEGylation at the N-terminus, side chain, and C-terminus of a potent analog of growth hormone-releasing factor has been performed through solid-phase synthesis [Felix, et al. (1995) Int. J. Peptide Protein Res. 46:253]. Another site-specific method involves attaching a peptide to extremities of liposomal surface-grafted PEG chains in a site-specific manner through a reactive aldehyde group at the N-terminus generated by sodium periodate oxidation of N-terminal threonine [Zalipsky, et al. (1995) Bioconj. Chem. 6:705]. However, this method is limited to polypeptides with N-terminal serine or threonine residues.

In one method, selective N-terminal PEGylation may be accomplished by reductive alkylation which exploits differential reactivity of different types of primary amino groups (lysine versus the N-terminal) available for derivatization in a particular peptide or spacer moiety. Under the appropriate reaction conditions, a carbonyl group containing PEG is selective attached to the N-terminus of a peptide or spacer. For example, one may selectively N-terminally PEGylate the protein by performing the reaction at a pH which exploits the pK$_a$ differences between the ε-amino groups of a lysine residue and the α-amino group of the N-terminal residue of the peptide or spacer. By such selective attachment, PEGylation takes place predominantly at the N-terminus of the protein, with no significant modification of other reactive groups (e.g., lysine side chain amino groups). Using reductive alkylation, the PEG should have a single reactive aldehyde for coupling to the protein (e.g., PEG proprionaldehyde may be used).

Site-specific mutagenesis is a further approach which may be used to prepare peptides for site-specific polymer attachment. By this method, the amino acid sequence of a peptide is designed to incorporate an appropriate reactive group at the desired position within the peptide. For example, WO 90/12874 describes the site-directed PEGylation of proteins modified by the insertion of cysteine residues or the substitution of other residues for cysteine residues. This publication also describes the preparation of mPEG-erythropoietin ("mPEG-EPO") by reacting a cysteine-specific mPEG derivative with a recombinantly introduced cysteine residue on EPO.

Where the PEG moiety is attached to a spacer moiety or a linker moiety, similar attachment methods may be used. In this case, the linker or spacer contains a reactive group and an activated PEG molecule containing the appropriate complementary reactive group is used to effect covalent attachment. In preferred embodiments the linker or spacer reactive group is a terminal reactive group (i.e., positioned at the terminus of the linker or spacer).

Peptides, peptide dimers and other peptide-based molecules of the invention can be attached to water-soluble polymers (e.g., PEG) using any of a variety of chemistries to link the water-soluble polymer(s) to the receptor-binding portion of the molecule (e.g., peptide+spacer). A typical embodiment employs a single attachment junction for covalent attachment of the water soluble polymer(s) to the receptor-binding portion, however in alternative embodiments multiple attachment junctions may be used, including further variations wherein different species of water-soluble polymer are attached to the receptor-binding portion at distinct attachment junctions, which may include covalent attachment junction(s) to the spacer and/or to one or both peptide chains. In some embodiments, the dimer or higher order multimer will comprise distinct species of peptide chain (i.e., a heterodimer or other heteromultimer). By way of example and not limitation, a dimer may comprise a first peptide chain having a PEG attachment junction and the second peptide chain may either lack a PEG attachment junction or utilize a different linkage chemistry than the first peptide chain and in some variations the spacer may contain or lack a PEG attachment junction and said spacer, if PEGylated, may utilize a linkage chemistry different than that of the first and/or second peptide chains. An alternative embodiment employs a PEG attached to the spacer portion of the receptor-binding portion and a different water-soluble polymer (e.g., a carbohydrate) conjugated to a side chain of one of the amino acids of the peptide portion of the molecule.

A wide variety of polyethylene glycol (PEG) species may be used for PEGylation of the receptor-binding portion (peptides+spacer). Substantially any suitable reactive PEG reagent can be used. In preferred embodiments, the reactive PEG reagent will result in formation of a carbamate or amide bond upon conjugation to the receptor-binding portion. Suitable reactive PEG species include, but are not limited to, those which are available for sale in the Drug Delivery Systems catalog (2003) of NOF Corporation (Yebisu Garden Place Tower, 20-3 Ebisu 4-chome, Shibuya-ku, Tokyo 150-6019) and the Molecular Engineering catalog (2003) of Nektar Therapeutics (490 Discovery Drive, Huntsville, Ala. 35806). For example and not limitation, the following PEG reagents are often preferred in various embodiments: $mPEG_2$-NHS, $mPEG_2$-ALD, multi-Arm PEG, $mPEG(MAL)_2$, mPEG2 (MAL), $mPEG$-$NH_2$, mPEG-SPA, mPEG-SBA, mPEG-thioesters, mPEG-Double Esters, mPEG-BTC, mPEG-ButyrALD, mPEG-ACET, heterofunctional PEGs (NH2-PEG-COOH, Boc-PEG-NHS, Fmoc-PEG-NHS, NHS-PEG-VS, NHS-PEG-MAL), PEG acrylates (ACRL-PEG-NHS), PEG-phospholipids (e.g., mPEG-DSPE), multiarmed PEGs of the SUNBRITE series including the GL series of glycerine-based PEGs activated by a chemistry chosen by those skilled in the art, any of the SUNBRITE activated PEGs (including but not limited to carboxyl-PEGs, p-NP-PEGs, Tresyl-PEGs, aldehyde PEGs, acetal-PEGs, amino-PEGs, thiol-PEGs, maleimido-PEGs, hydroxyl-PEG-amine, amino-PEG-COOH, hydroxyl-PEG-aldehyde, carboxylic anhydride type-PEG, functionalized PEG-phospholipid, and other similar and/or suitable reactive PEGs as selected by those skilled in the art for their particular application and usage.

Peptide Moiety

Any peptides derived from various animals including humans, microorganisms or plants and those produced by genetic engineering and by synthesis may be employed as the peptide moiety. Examples include peptides that bind to EPO-R; peptides that bind to TPO-R, cytokines such as various interferons (e.g. interferon-α, interferon-β, interferon-γ), interleukin-2 and interleukin-3, hormones such as insulin, growth hormone-releasing factor (GRF), calcitonin, calcitonin gene related peptide (CGRP), atrial natriuretic peptide (ANP), vasopressin, corticotropin-releasing factor (CRF), vasoactive intestinal peptide (VIP), secretin, α-melanocyte-stimulating hormone (α-MSH), adrenocorticotropic hormone (ACTH), cholecystokinin (CCK), glucagon, parathyroid hormone (PTH), somatostatin, endothelin, substance P, dynorphin, oxytocin and growth hormone-releasing peptide [GHRP, e.g. Endocrinology, 114, 1537 (1984)], growth factors such as growth hormone (GH), insulin-like growth factor (IGF-I, IGF-II), -nerve growth factor (β-NGF), basic fibroblast growth factor (bFGF), transforming growth factor, erythropoietin, granulocyte colony-stimulating factor (G-CSF), granulocyte macrophage colony-stimulating factor (GM-CSF), platelet-derived growth factor (PDGF) and epidermal growth factor (EGF), enzymes such as tissue plasminogen activator (t-PA), elastase, superoxide dismutase (SOD) bilirubin oxydase, catalase, uricase and asparaginase, other proteins such as ubiquitin, islet activating protein (IAP), serum thymic factor (STF), peptide-T and trypsin inhibitor, and derivatives thereof.

Preferably, the peptide moiety comprises one or more peptides, the length of each peptide is less than 50 amino acids, more preferably between about 10 and 25 amino acids, and most preferably between about 12-18 amino acids.

In one preferred embodiment, the peptide moiety is selected from peptides that bind to EPO-R such as those disclosed in (e.g. those disclosed in U.S. Pat. Nos. 5,773,569; 5,830,851; and 5,986,047 to Wrighton, et al.; PCT Pub. No. WO 96/40749 to Wrighton, et al.; U.S. Pat. No. 5,767,078 and PCT Pub. No. 96/40772 to Johnson and Zivin; PCT Pub. No. WO 01/38342 to Balu; and WO 01/91780 to Smith-Swintosky, et al. Still other exemplary EPO-R binding peptides which may be used as the peptide moiety in the present invention are described in U.S. Provisional Application Ser. No. 60/470,245 filed May 12, 2003. Still other exemplary EPO-R binding peptides which may be used as the peptide moiety in the present invention are described in U.S. Provisional Application Ser. Nos. 60/469,993 filed May 12, 2003. Yet still other exemplary EPO-R binding peptides which may be used as the peptide moiety in the present invention are described in U.S. Provisional Application Ser. No. 60/470,244 filed May 12, 2003.

In another preferred embodiment, the peptide moiety is selected from peptides which bind to thrombopoietin-receptors ("TPO-R"). Non-limiting examples of such TPO-R binding peptides include those disclosed in U.S. Pat. Nos. 6,552,008, 6,506,362, 6,498,155, 6,465,430, 6,333,031, 6,251,864, 6,121,238, 6,083,913, 5,932,546, 5,869,451, 5,683,983, 5,677,280, 5,668,110 and 5,654,276; and published U.S. Patent Applications 2003/0083361, 2003/0009018, 2002/0177166 and 2002/0160013.

In one embodiment, the peptide moiety is a monomeric peptide of 10 to 40 or more amino acid residues in length and having the sequence $X_3X_4X_5GPX_6TWX_7X_8$ (SEQ ID NO:7) where each amino acid is indicated by standard one letter abbreviation; $X_3$ is C; $X_4$ is R, H, L, or W; $X_5$ is M, F, or I; $X_6$ is independently selected from any one of the 20 genetically coded L-amino acids; $X_7$ is D, E, I, L, or V; and $X_8$ is C, which bind and activate the erythropoietin receptor (EPO-R) or otherwise act as an EPO agonist.

In another embodiment, the peptide moiety is a monomeric peptide of 17 to about 40 amino acids in length that comprise the core amino acid sequence LYACHMGPITX$_1$VCQPLR (SEQ ID NO:8), where each amino acid is indicated by standard one letter abbreviation; and $X_1$ is tryptophan (W), 1-naphthylalanine (1-nal), or 2-naphthylalanine (2-nal).

In yet another embodiment, the peptide moiety comprises one or more TPO-R binding peptides with sequence such as Ac-Ile-Glu-Gly-Pro-Thr-Leu-Arg-Gln-Nal(1)-Leu-Ala-Ala-Arg-Sar (SEQ ID NO:5), or Ac-Ile-Glu-Gly-Pro-Thr-Leu-Arg-Gln-Trp-Leu-Ala-Ala-Arg-Sar (SEQ ID NO:6).

In one embodiment, the peptide moiety is attached directly to the spacer moiety.

In another embodiment, the peptide moiety is attached to the spacer moiety via a linker.

According to some embodiments of this invention, two or more, and preferably between two to six amino acid residues, independently selected from any of the 20 genetically coded L-amino acids or the stereoisomeric D-amino acids, will be coupled to either or both ends of the core sequences described above. For example, the sequence GG will often be appended to either or both termini of the core sequences for ease in synthesis of the peptides. The present invention also provides conjugates of these peptides and derivatives and peptidomimetics of the peptides that retain the property of EPO-R binding.

Stereoisomers (e.g., D-amino acids) of the twenty conventional amino acids, unnatural amino acids such as a,a-disubstituted amino acids, N-alkyl amino acids, lactic acid, and other unconventional amino acids may also be suitable components for compounds of the present invention. Examples of unconventional amino acids include, but are not limited to: β-alanine, 3-pyridylalanine, 4-hydroxyproline, O-phosphoserine, N-methylglycine, N-acetylserine, N-formylmethionine, 3-methylhistidine, 5-hydroxylysine, nor-leucine, 1- or 2-naphthylalanine, sarcosine, and other similar amino acids and imino acids.

In preferred embodiments, the peptide moieties of the invention contain an intramolecular disulfide bond between the two cysteine residues of the core sequence. For example:

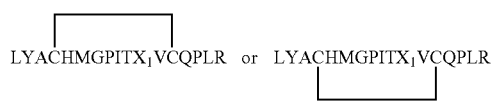

Dimeric and Oligomeric Peptides

The preferred embodiment, the monomeric peptide moieties of the present invention are dimerized or oligomerized to form dimers or oligomers. Moreover, such dimers and other multimers may be heterodimers or heteromultimers.

In one embodiment, the peptide monomers of the invention may be oligomerized using the biotin/streptavidin system. Biotinylated analogs of peptide monomers may be synthesized by standard techniques. For example, the peptide monomers may be C-terminally biotinylated. These biotinylated monomers are then oligomerized by incubation with streptavidin [e.g., at a 4:1 molar ratio at room temperature in phosphate buffered saline (PBS) or HEPES-buffered RPMI medium (Invitrogen) for 1 hour]. In a variation of this embodiment, biotinylated peptide monomers may be oligomerized by incubation with any one of a number of commercially available anti-biotin antibodies [e.g., goat anti-biotin IgG from Kirkegaard & Perry Laboratories, Inc. (Washington, D.C.)].

Linkers

In preferred embodiments, the peptide monomers of the invention are dimerized by covalent attachment to at least one linker moiety. The linker ($L_K$) moiety is preferably, although not necessarily, a nitrogen-based linker. The linker moiety is most preferably a trifunctional linker optionally terminated with one or two —CO— linkages. In a preferred embodiment of the present invention the linker $L_K$ comprises the following structure:

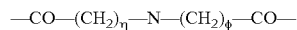

wherein η and φ are each integers whose values are independently selected, N is covalently bonded to Y of the spacer moiety, and Y of the spacer moiety is CO. Most preferably the linker bridges the C-terminal of two peptide monomers, by simultaneous attachment to the C-terminal amino acid of each monomer. For example, when the linker $L_K$ forms an amide bond with the ε-amino group of the C-terminal lysine residue of the first and second peptide monomer the dimer may be illustrated structurally as shown in Formula III, and summarized as shown in Formula IV:

Formula III

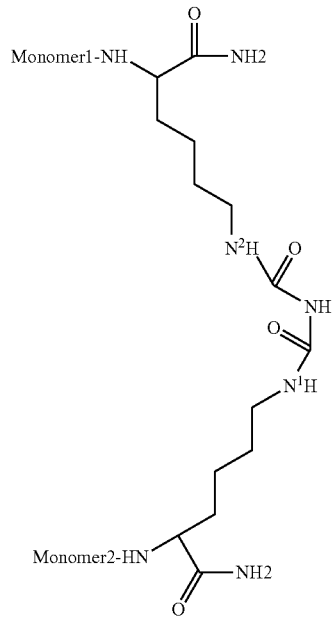

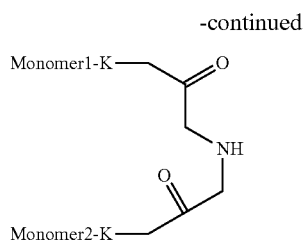

Formula IV

In Formula IV, $N^2$ represents the nitrogen atom of lysine's ε-amino group and $N^1$ represents the nitrogen atom of lysine's ε-amino group. The dimeric structure can be written as [peptide-Lys]$_2$-L$_K$ to denote a peptide containing a lysine residue in which the ε-amino group of the C-terminal lysine residue is bound to the linker moiety, [peptide-Lys, disulfide]$_2$-L$_K$ to denote a peptide containing a lysine residue in which the ε-amino group of the C-terminal lysine residue is bound to the linker moiety with each peptide containing an intramolecular disulfide loop, [peptide-Lys, disulfide]$_2$-L$_K$-Spacer-PEG to denote a peptide containing a lysine residue in which the ε-amino group of the C-terminal lysine residue is bound to the linker moiety with each protein containing an intramolecular disulfide loop and a spacer molecular forming a covalent linkage between the C-terminus of lysine and a PEG moiety, or [peptide-Lys, disulfide]$_2$-L$_K$-Spacer-PEG$_2$ to denote a peptide containing a lysine residue in which the ε-amino group of the C-terminal lysine residue is bound to the linker moiety with each protein containing an intramolecular disulfide loop and a spacer molecular forming two covalent linkage between the C-terminus of lysine and a PEG moiety.

In another preferred embodiment the linker is a lysine residue or a lysine amide (a lysine residue wherein the carboxyl group has been converted to an amide moiety-CONH$_2$). More preferably, the linker brides the C-termini of two peptide monomers, by simultaneous attachment to the C-terminal amino acid of each monomer. For example, when the C-terminal linker L$_K$ is a lysine amide the dimer may be illustrated structurally as shown in Formula V, and summarized as shown in Formula VI:

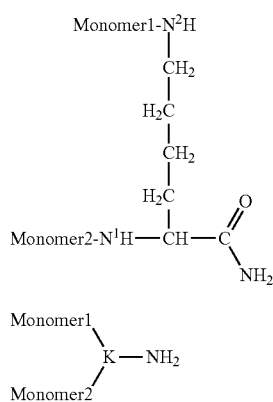

Formula V

Formula VI

In Formula V, $N^2$ represents the nitrogen atom of lysine's ε-amino group and $N^1$ represents the nitrogen atom of lysine's α-amino group. The dimeric structure can be written as [peptide]$_2$-L$_K$ to denote a peptide bound to both the α and ε amino groups of linker moiety comprising lysine, or [Ac-peptide]$_2$-L$_K$ to denote an N-terminally acetylated peptide bound to both the α and ε amino groups of a linker moiety comprising lysine, or [Ac-peptide, disulfide]$_2$-L$_K$ to denote an N-terminally acetylated peptide bound to both the α and ε amino groups of a linker moiety comprising lysine with each peptide containing an intramolecular disulfide loop, or [Ac-peptide, disulfide]$_2$-L$_K$-spacer-PEG to denote an N-terminally acetylated peptide bound to both the α and ε amino groups of a linker moiety comprising lysine with each peptide containing an intramolecular disulfide loop and a spacer molecule forming a covalent linkage between the C-terminus of a linker moiety and a PEG moiety.

Generally, although not necessarily, peptide dimers dimerized by a technique other than formation of intermolecular disulfide bonds, will also contain one or more disulfide bonds between cysteine residues of the peptide monomers. For example, the two monomers may be cross-linked by one or more intermolecular disulfide bonds. Preferably, the two monomers contain at least one intramolecular disulfide bond. Most preferably, both monomers of a peptide dimer contain an intramolecular disulfide bond, such that each monomer contains a cyclic group.

Peptide Modification

One can also modify the amino and/or carboxy termini of the peptide compounds of the invention to produce other compounds of the invention. Amino terminus modifications include methylation (i.e., —NHCH$_3$ or —N(CH$_3$)$_2$), acetylation (e.g., with acetic acid or a halogenated derivative thereof such as α-chloroacetic acid, α-bromoacetic acid, or α-iodoacetic acid), adding a benzyloxycarbonyl (Cbz) group, or blocking the amino terminus with any blocking group containing a carboxylate functionality defined by RCOO— or sulfonyl functionality defined by R—SO$_2$—, where R is selected from the group consisting of alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the peptide compound. In preferred embodiments, the N-terminus is acetylated. In most preferred embodiments an N-terminal glycine is acetylated to yield N-acetylglycine (AcG).

Carboxy terminus modifications include replacing the free acid with a carboxamide group or forming a cyclic lactam at the carboxy terminus to introduce structural constraints. One can also cyclize the peptides of the invention, or incorporate a desamino or descarboxy residue at the termini of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

One can replace the naturally occurring side chains of the 20 genetically encoded amino acids (or the stereoisomeric D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic. In particular, proline analogues in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify the peptide moieties by phosphorylation, and other methods [e.g., as described in Hruby, et al. (1990) Biochem J. 268:249-262].

The peptide moieties of the invention may also serve as structural models for non-peptidic compounds with similar biological activity. Those of skill in the art recognize that a variety of techniques are available for constructing compounds with the same or similar desired biological activity as the lead peptide compound, but with more favorable activity than the lead with respect to solubility, stability, and susceptibility to hydrolysis and proteolysis [See, Morgan and Gainor (1989) Ann. Rep. Med. Chem. 24:243-252]. These techniques include replacing the peptide backbone with a backbone composed of phosphonates, amidates, carbamates, sulfonamides, secondary amines, and N-methylamino acids.

Pharmaceutical Compositions

In another aspect of the present invention, pharmaceutical compositions of the above PEG-modified peptide based compounds are provided. Conditions alleviated or modulated by the administration of such compositions include those indicated above. Such pharmaceutical compositions may be for administration by oral, parenteral (intramuscular, intraperitoneal, intravenous (IV) or subcutaneous injection), transdermal (either passively or using iontophoresis or electroporation), transmucosal (nasal, vaginal, rectal, or sublingual) routes of administration or using bioerodible inserts and can be formulated in dosage forms appropriate for each route of administration. In general, comprehended by the invention are pharmaceutical compositions comprising effective amounts of a therapeutic peptide (e.g. peptides that bind to EPO-R), with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form.

Oral Delivery

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets, pellets, powders, or granules. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the EPO-R agonist peptides (or chemically modified forms thereof) and inert ingredients which allow for protection against the stomach environment, and release of the biologically active material in the intestine.

Also contemplated for use herein are liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

The peptides may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. As discussed above, PEGylation is a preferred chemical modification for pharmaceutical usage. Other moieties that may be used include: propylene glycol, copolymers of ethylene glycol and propylene glycol, carboxymethyl cellulose, dextran, fatty acids (e.g. myristic acid), peptides [see Dennis, M. S. et al J. Biol. Chem. 2002, 277, 35035], polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in *Enzymes as Drugs*. Hocenberg and Roberts, eds. (Wiley-Interscience: New York, N.Y.) pp. 367-383; and Newmark, et al. (1982) J. Appl. Biochem. 4:185-189].

For oral formulations, the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the peptide (or derivative) or by release of the peptide (or derivative) beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used.

The peptide (or derivative) can be included in the formulation as fine multiparticulates in the form of granules or pellets of particle size about 1 mm. The formulation of the material for capsule administration could also be as a powder, lightly compressed plugs, or even as tablets. These therapeutics could be prepared by compression.

Colorants and/or flavoring agents may also be included. For example, the peptide (or derivative) may be formulated (such as by liposome or microsphere encapsulation) and then further contained within an edible product, such as a refrigerated beverage containing colorants and flavoring agents.

One may dilute or increase the volume of the peptide (or derivative) with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. The disintegrants may also be insoluble cationic exchange resins. Powdered gums may be used as disintegrants and as binders, and can include powdered gums such as agar, Karaya or tragacanth. Alginic acid and its sodium salt are also useful as disintegrants.

Binders may be used to hold the peptide (or derivative) agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the peptide (or derivative).

An antifrictional agent may be included in the formulation of the peptide (or derivative) to prevent sticking during the formulation process. Lubricants may be used as a layer between the peptide (or derivative) and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the peptide (or derivative) into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the peptide (or derivative) are for instance the fatty acids oleic acid, linoleic acid and linolenic acid.

Controlled release oral formulations may be desirable. The peptide (or derivative) could be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release is by a method based on the Oros therapeutic system (Alza Corp.), i.e. the drug is enclosed in a semipermeable membrane which allows water to enter and push drug out through a single small opening due to osmotic effects.

Other coatings may be used for the formulation. These include a variety of sugars which could be applied in a coating pan. The peptide (or derivative) could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Parenteral Delivery

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Rectal or Vaginal Delivery

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

Pulmonary Delivery

Also contemplated herein is pulmonary delivery of the EPO-R agonist peptides (or derivatives thereof). The peptide (or derivative) is delivered to the lungs of a mammal while inhaling and traverses across the lung epithelial lining to the blood stream [see, e.g., Adjei, et al. (1990) Pharmaceutical Research 7:565-569; Adjei, et al. (1990) Int. J. Pharmaceutics 63:135-144 (leuprolide acetate); Braquet, et al. (1989) J. Cardiovascular Pharmacology 13(sup5):143-146 (endothelin-1); Hubbard, et al. (1989) Annals of Internal Medicine, Vol. III, pp. 206-212 (α1-antitrypsin); Smith, et al. (1989) J. Clin. Invest. 84:1145-1146 (α-1-proteinase); Oswein, et al. (1990) "Aerosolization of Proteins", Proceedings of Symposium on Respiratory Drug Delivery II Keystone, Colo. (recombinant human growth hormone); Debs, et al. (1988) J. Immunol. 140:3482-3488 (interferon-γ and tumor necrosis factor α); and U.S. Pat. No. 5,284,656 to Platz, et al. (granulocyte colony stimulating factor). A method and composition for pulmonary delivery of drugs for systemic effect is described in U.S. Pat. No. 5,451,569 to Wong, et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, NC); and the Spinhaler powder inhaler (Fisons Corp., Bedford, Mass.).

All such devices require the use of formulations suitable for the dispensing of peptide (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified peptides may also be prepared in different formulations depending on the type of chemical modification or the type of device employed.

Formulations suitable for use with a nebulizer, either jet or ultrasonic, will typically comprise peptide (or derivative) dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the peptide (or derivative) caused by atomization of the solution in forming the aerosol.

Formulations for use with a metered-dose inhaler device will generally comprise a finely divided powder containing the peptide (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing peptide (or derivative) and may also include a bulking agent, such as lactose, sorbitol, sucrose, or mannitol in amounts which facilitate dispersal of the powder from the device, e.g., 50 to 90% by weight of the formulation. The peptide (or derivative) should most advantageously be prepared in particulate form with an average particle size of less than 10 mm (or microns), most preferably 0.5 to 5 mm, for most effective delivery to the distal lung.

Nasal Delivery

Nasal delivery of the EPO-R agonist peptides (or derivatives) is also contemplated. Nasal delivery allows the passage of the peptide to the blood stream directly after administering the therapeutic product to the nose, without the necessity for deposition of the product in the lung. Formulations for nasal delivery include those with dextran or cyclodextran.

Dosages

For all of the peptide compounds, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of between 0.001 to 10 mg/kg of body weight daily are administered to mammals. Generally, for intravenous injection or infusion dosage may be lower. The dosing schedule may vary, depending on the circulation half-life, and the formulation used.

The peptides of the present invention (or their derivatives) may be administered in conjunction with one or more additional active ingredients or pharmaceutical compositions.

EXAMPLES

The following Examples illustrate the invention, but are not limiting.

Example 1

Synthesis of H-TAP-Boc Molecule

Step A: Synthesis of Cbz-TAP

FIG. 1A illustrates synthesis of Cbz-TAP from TAP. A solution of TAP (10 g, 67.47 mmol, purchased from Aldrich Chemical Co.) in anhydrous dichloromethane (DCM) (100 ml) was cooled to 0° C. A solution of benzyl chloroformate (Cbz-Cl, Cbz=carboxybenzyloxy) (4.82 ml, 33.7 mmol) in anhydrous DCM (50 ml) was added slowly to the TAP solution through a dropping funnel over a period of 6-7 hrs while the temperature of the reaction mixture was maintained at 0° C. throughout. The resulting mixture then allowed to warm to room temperature (~25° C.). After another 16 hrs, the DCM was removed under vacuum and the residue was partitioned between 3N HCl and ether. The aqueous layers were collected and neutralized with 50% aq. NaOH to pH 8-9 and extracted with ethyl acetate. The ethyl acetate layer was dried over anhydrous $Na_2SO_4$, and then concentrated under vacuum to provide the crude mono-Cbz-TAP (5 g, about 50% yield). This compound was used for the reaction in Step B without further purification.

Step B: Synthesis of Cbz-TAP-Boc

Figure 1B:
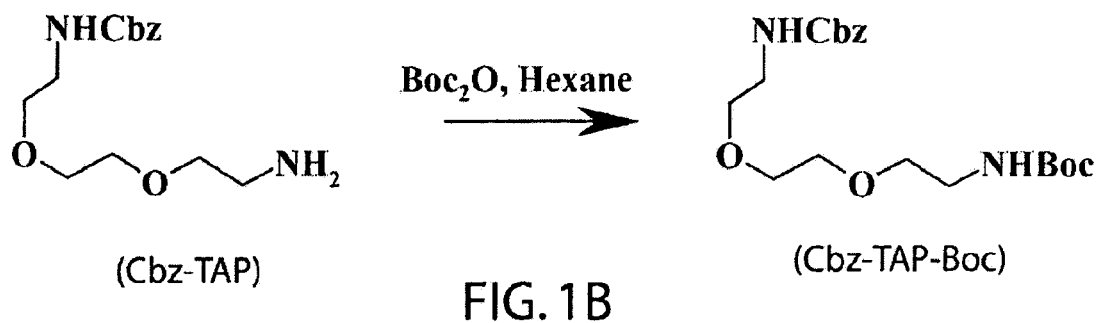

FIG. 1B illustrates synthesis of Cbz-TAP-Boc from Cbz-TAP. $Boc_2O$ (3.86 g, 17.7 mmol, Boc=tert-butoxycarbonyl) was added to a vigorously stirred suspension of the Cbz-TAP (5 g, 17.7 mmol) in hexane (25 ml). Stirring continued at room temperature overnight. The reaction mixture was diluted with DCM (25 ml) and washed with 10% aq. citric acid (2×), water (2×) and brine. The organic layer was dried over anhydrous $Na_2SO_4$ and concentrated under vacuum. The crude product (yield 5 g) was used directly in the reaction in Step C.

Step C: Synthesis of Boc-TAP

Figure 1C:
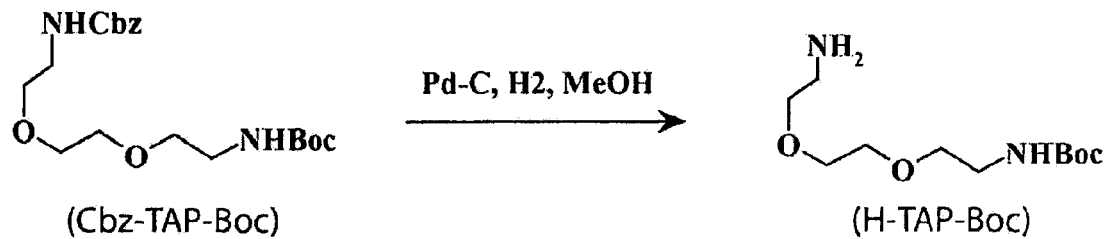

FIG. 1C illustrates synthesis of H-TAP-Boc from Cbz-TAP-Boc. The crude Cbz-TAP-Boc from Step B was dissolved in methanol (25 ml) and hydrogenated in presence of 5% Pd on Carbon (5% w/w) under balloon pressure for 16 hrs. The mixture was filtered, washed with methanol and the filtrate concentrated under vacuum to provide the crude H-TAP-Boc product (yield 3.7 g).

The overall yield after Steps A-C is approximately 44% (calculated based on the amount of Cbz-Cl used).

Example 2

Attaching Spacer to Peptide with C-Terminus

Figure 2:
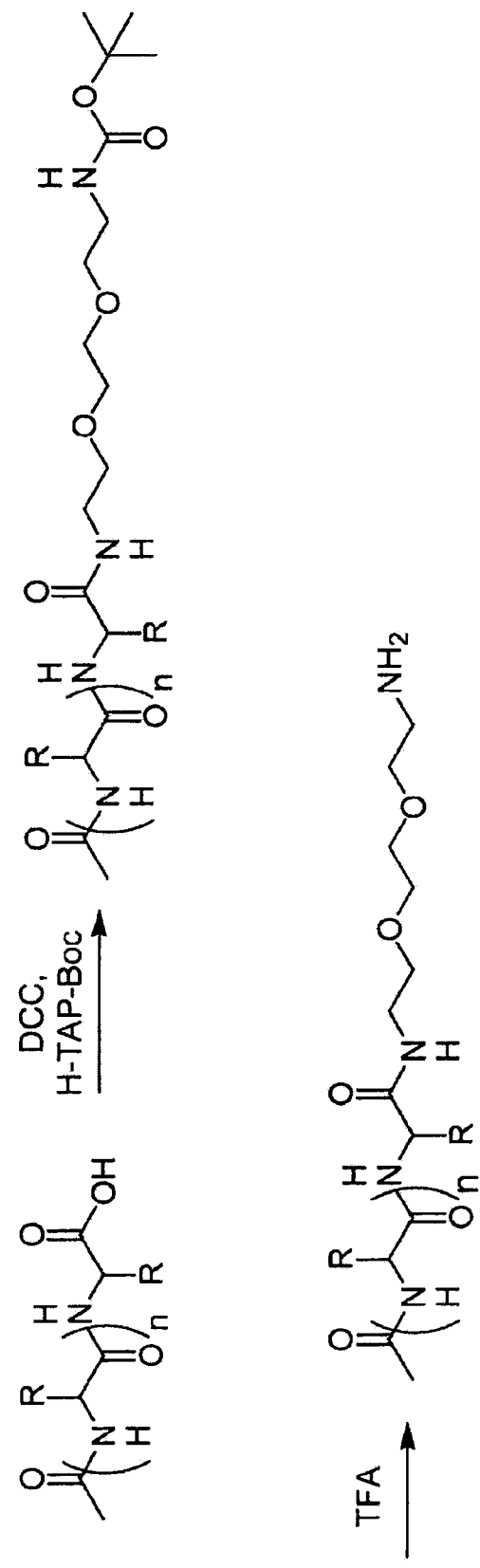
FIG. 2 shows a reaction scheme illustrating how to attach a spacer to a peptide with C-terminus.

The reaction scheme in FIG. 2 illustrates how to attach a spacer to a peptide with C-terminus.
H-TAP-Boc was prepared according to Example 1. DCC in FIG. 2 is N,N'-Dicyclohexylcarbodiimide.

Example 3

Attaching Spacer to Peptide with Free Side-Chain Acid

Figure 3:
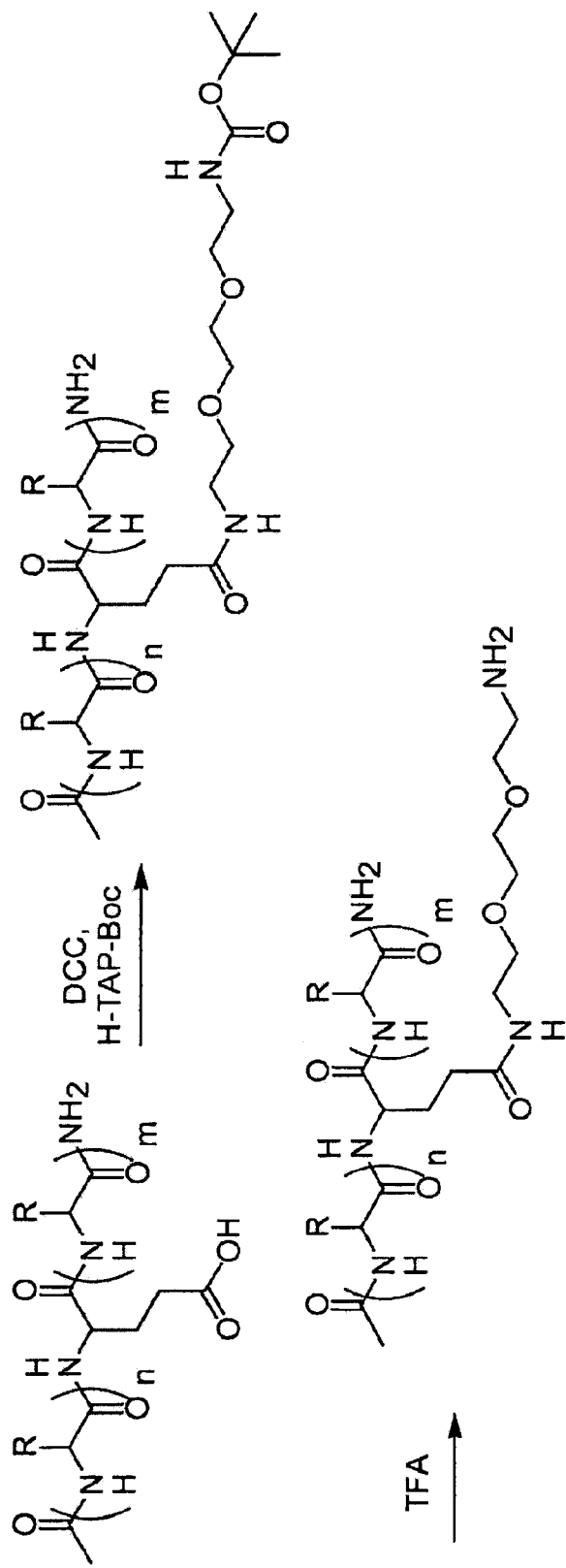
FIG. 3 shows a reaction scheme illustrating how to attach a spacer to a peptide with a free side chain.

The reaction scheme in FIG. 3 illustrates how to attach a spacer to a peptide with a free side-chain acid.
TFA in FIG. 3 is trifluoroacetic acid.

Example 4

PEGylation of Peptide, with mPEG-NPC

Figure 4A:
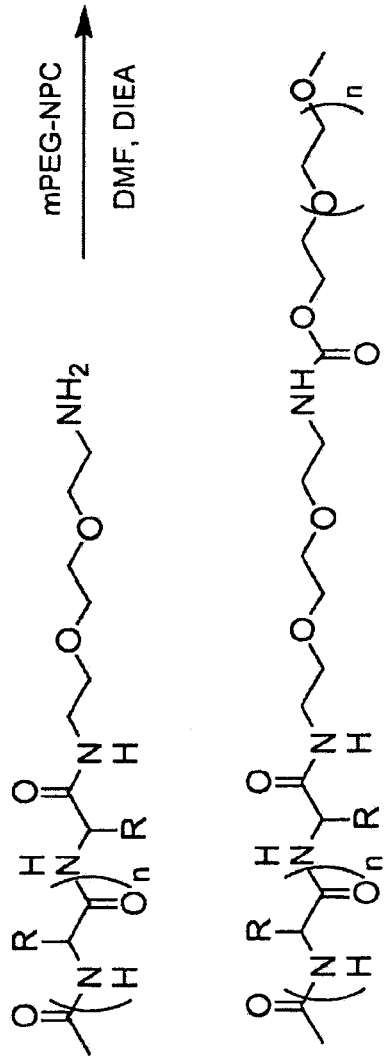
FIG. 4A shows a reaction scheme for the PEGylation of peptide with mPEG-NPC, where the structure of mPEG-NPC is illustrated in FIG. 4B.
Figure 4B:
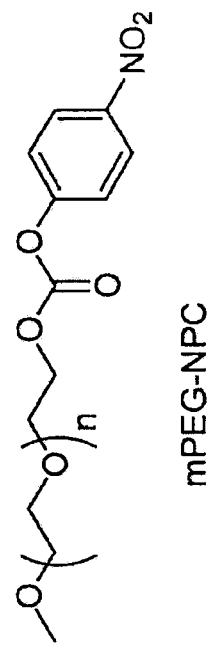

PEGylation of peptide with mPEG-NPC is illustrated in FIG. 4A, wherein mPEG-NPC has the structure illustrated in FIG. 4B.

Example 5

PEGylation of Peptide, with mPEG-SPA

Figure 5A:
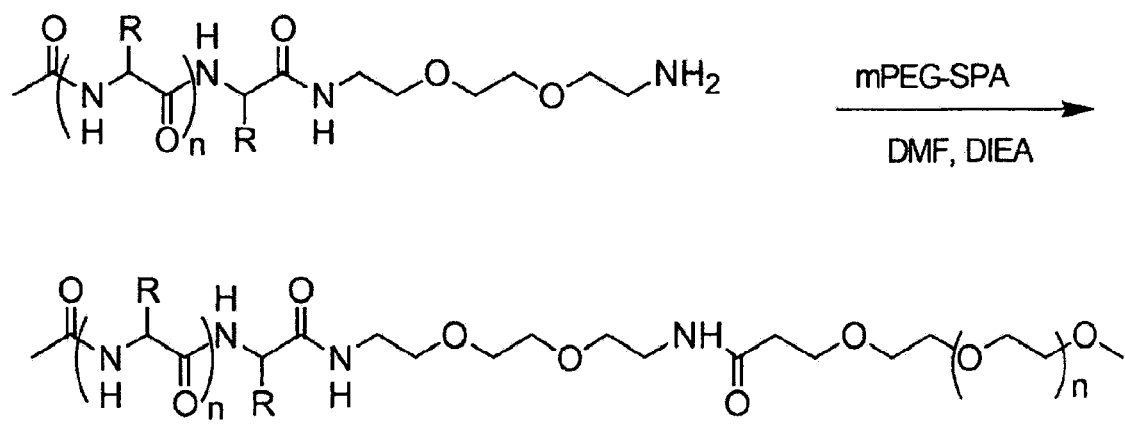
FIG. 5A shows a reaction scheme for PEGylation of a peptide with mPEG-SPA, where the structure of mPEG-SPA is illustrated in FIG. 5B.
Figure 5B:
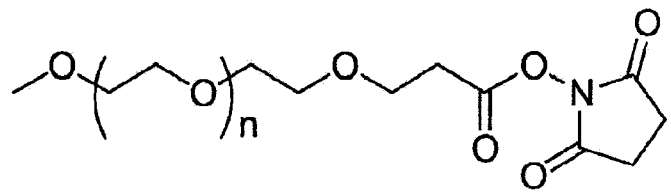

PEGylation of peptide with mPEG-SPA is illustrated in FIG. 5A, wherein mPEG-SPA has the structurev illustrated in FIG. 5B.

Example 6

Attaching Spacer and Synthesizing Peptide

Figure 6:
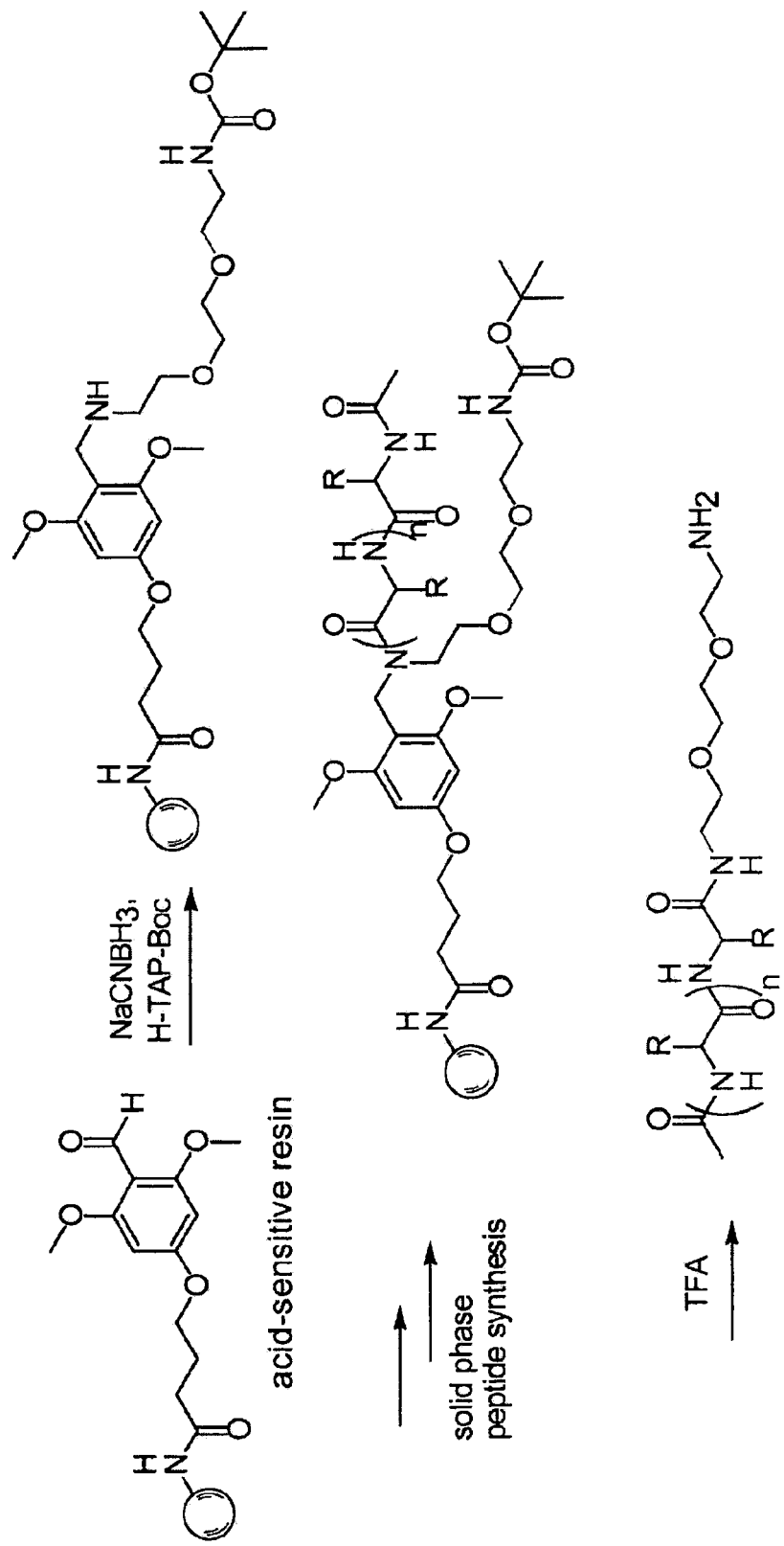
FIG. 6 shows a reaction scheme illustrating how to attach a spacer to a solid support and synthesize a peptide on such solid support.

The reaction scheme in FIG. 6 illustrates how to attach a spacer to on solid support and synthesize a peptide on such solid support.

Example 7

Synthesis of Peptide Dimer with Spacer, Attached to Resin

Step A: Synthesis of TentaGel-Linker

Figure 7A:
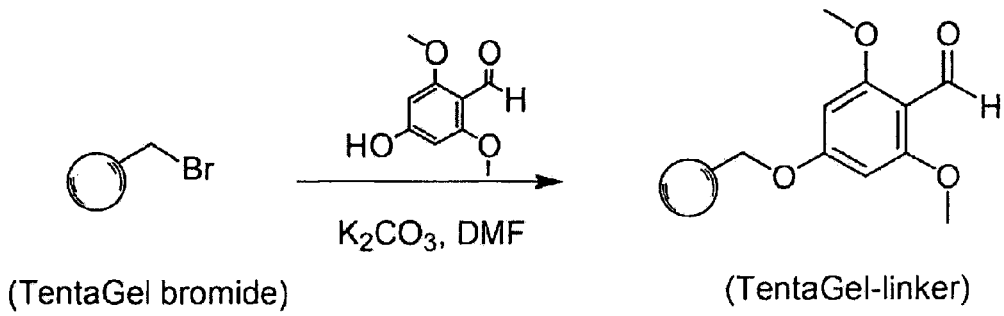
FIGS. 7A-7F show reaction schemes illustrating synthesis of a peptide dimer with spacer attached to a resin.

FIG. 7A shows synthesis of a TentaGel-linker from Tenta-Gel bromide. TentaGel bromide (2.5 g, 0.48 mmol/g, obtained from Rapp Polymere, Germany), phenolic linker (5 equivalent), and $K_2CO_3$ (5 equivalent) were heated in 20 mL of N,N-dimethylformamide (DMF) to 70° C. for 14 hrs. After cooling to room temperature, the resin was washed (0.1 N HCl, water, Acetonitrile (ACN), DMF, MeOH) and dried to give an amber-colored resin.

Step B: Synthesis of TentaGel-Linker-TAP(Boc)

Figure 7B:
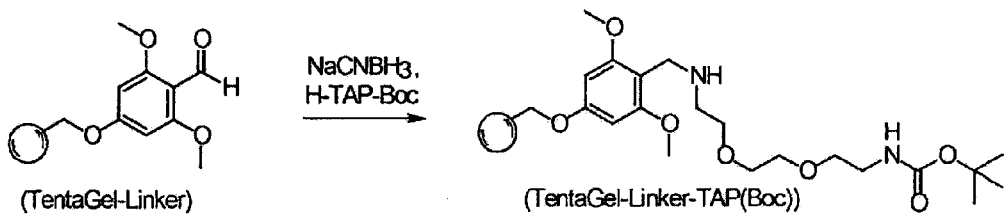

FIG. 7B shows synthesis of TentaGel-LinkerTAP(Boc) from TentaGel-linker. 2.5 g of the resin from Step A above and H-TAP-Boc (1.5 gms, 5 eq.) and glacial AcOH (34 µl, 5 eq.) was taken in a mixture of 1:1 MeOH/Tetrahydrofuran (THF) and shaken overnight. A 1M solution of sodium cyanoborohydride (5 eq.) in THF was added to the mixture and shaken for another 7 hrs. The resin was filtered washed (DMF, THF, 0.1 N HCl, water, MeOH) and dried. A small amount of the resin was benzoylated with benzyl chloride and diisopropylethylamine (DIEA) in DCM and cleaved with 70% trifluoroacetic acid (TFA)-DCM and checked by LCMS and HPLC.

Step C: Synthesis of TentaGel-Linker-TAP-Lys

Figure 7C:
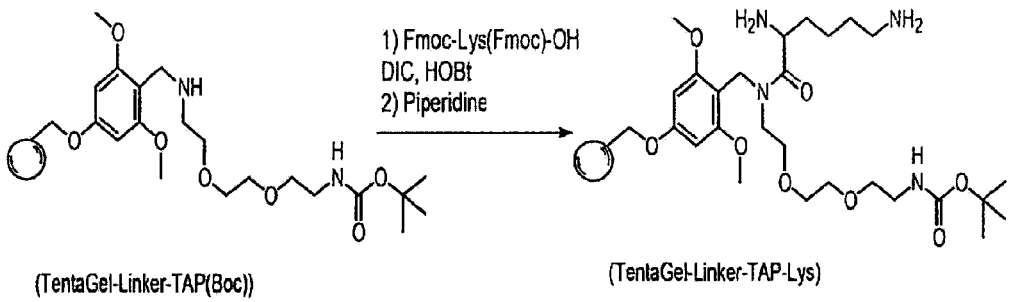

FIG. 7C shows synthesis of TentaGel-Linker-TAP-Lys from TentaGel-Linker-TAP(Boc). The resin from Step B above was treated with an activated solution of Fmoc-Lys (Fmoc)-OH (Fmoc=9-Fluorenylmethoxycarbonyl, prepared from 5 eq. of amino acid and 5 eq. of HATU (N,N,N',N'-Tetramethyl-O-(7-azabenzotriazol-1-yl)uronium hexafluorophosphate) dissolved at 0.5 M in DMF, followed by the addition of 10 eq. of DIEA) and gently shaken for 14 hrs. The resin was then washed (DMF, THF, DCM, MeOH) and dried to yield the protected resin. Residual amine groups were capped by treating the resin with a solution of 10% acetic anhydride, 20% pyridine in DCM for 20 minutes, followed by washing as above. The Fmoc groups were removed by gently shaking the resin in 30% piperideine in DMF for 20 minutes, followed by washing (DMF, THF, DCM, MeOH) and drying.

Step D: Synthesis of TentaGel-Linker-TAP-Lys(Peptide)$_2$

Figure 7D:
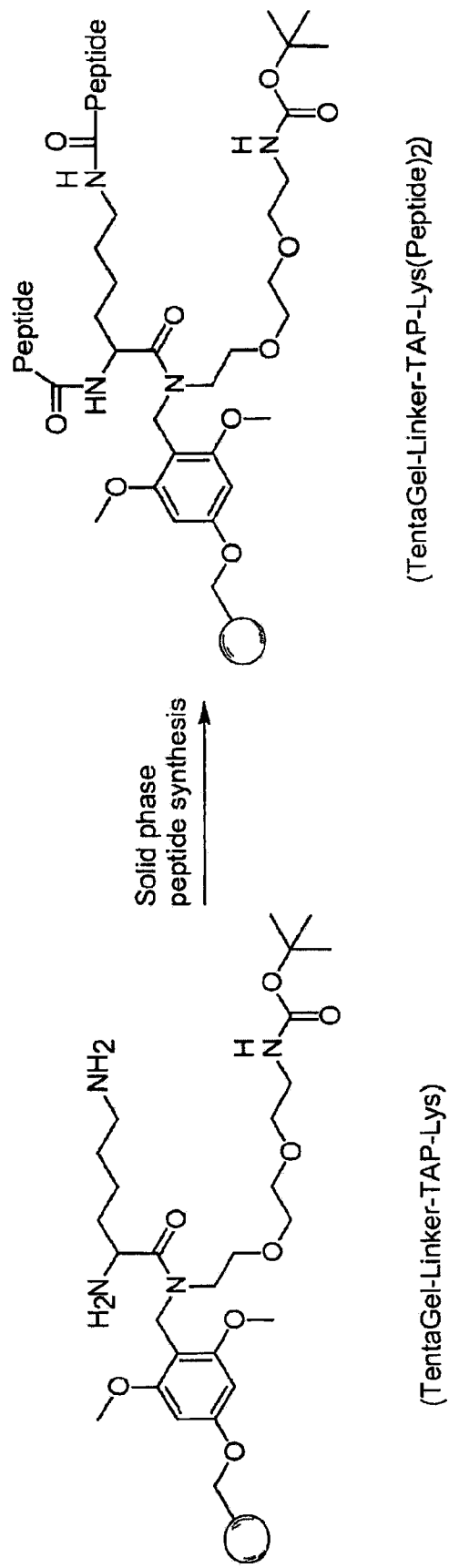

FIG. 7D shows synthesis of TentaGel-Linker-TAP-Lys (Peptide)$_2$ from TentaGel-Linker-TAP-Lys. The resin from Step C above was subjected to repeated cycles of Fmoc-amino acid couplings with HBTU/HOBt activation and Fmoc removal with piperidine to build both peptide chains simultaneously. This was conveniently carried out on an ABI 433 automated peptide synthesizer available from Applied Biosystems, Inc. After the final Fmoc removal, the terminal amine groups were acylated with acetic anhydride (10 eq.) and DIEA (20 eq.) in DMF for 20 minutes, followed by washing as above.

Step E: Cleavage from Resin

Figure 7E:
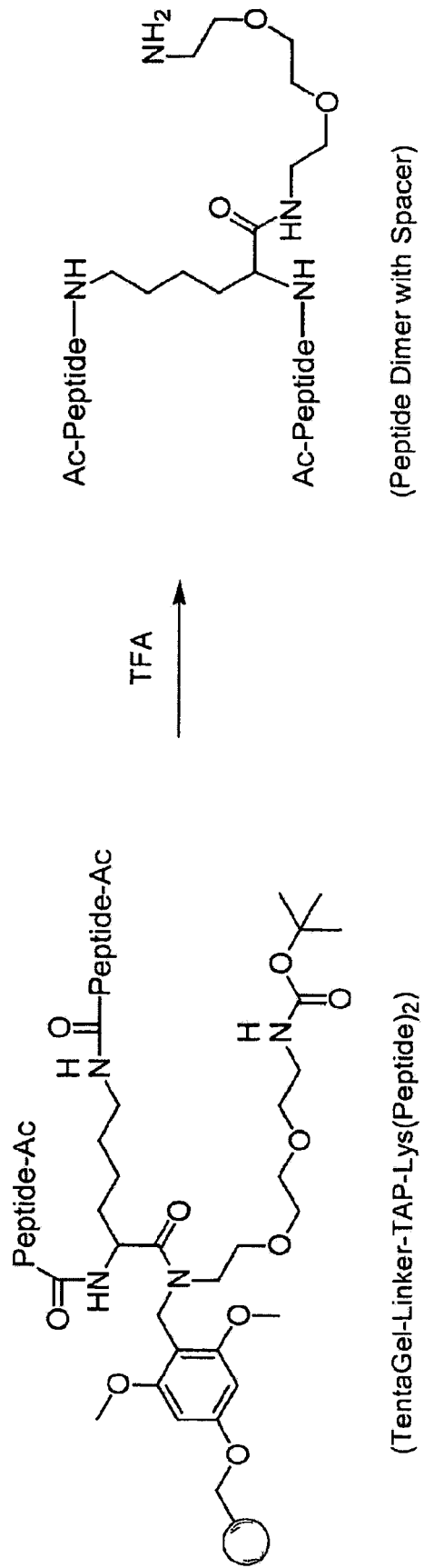

FIG. 7E shows cleavage of peptide dimer with spacer from resin. The resin from Step D above was suspended in a solution of TFA (82.5%), phenol (5%), ethanedithiol (2.5%), water (5%), and thioanisole (5%) for 3 hrs at room temperature. Alternative cleavage cocktails such as TFA (95%), water (2.5%), and triisopropylsilane (2.5%) can also be used. The TFA solution was cooled to 5° C. and poured into $Et_2O$ to precipitate the peptide. Filtration and drying under reduced pressure gave the desired peptide dimer with spacer. Purification via preparative HPLC with a C18 column yielded pure peptide dimer with spacer.

Step F: Oxidation

Figure 7F:
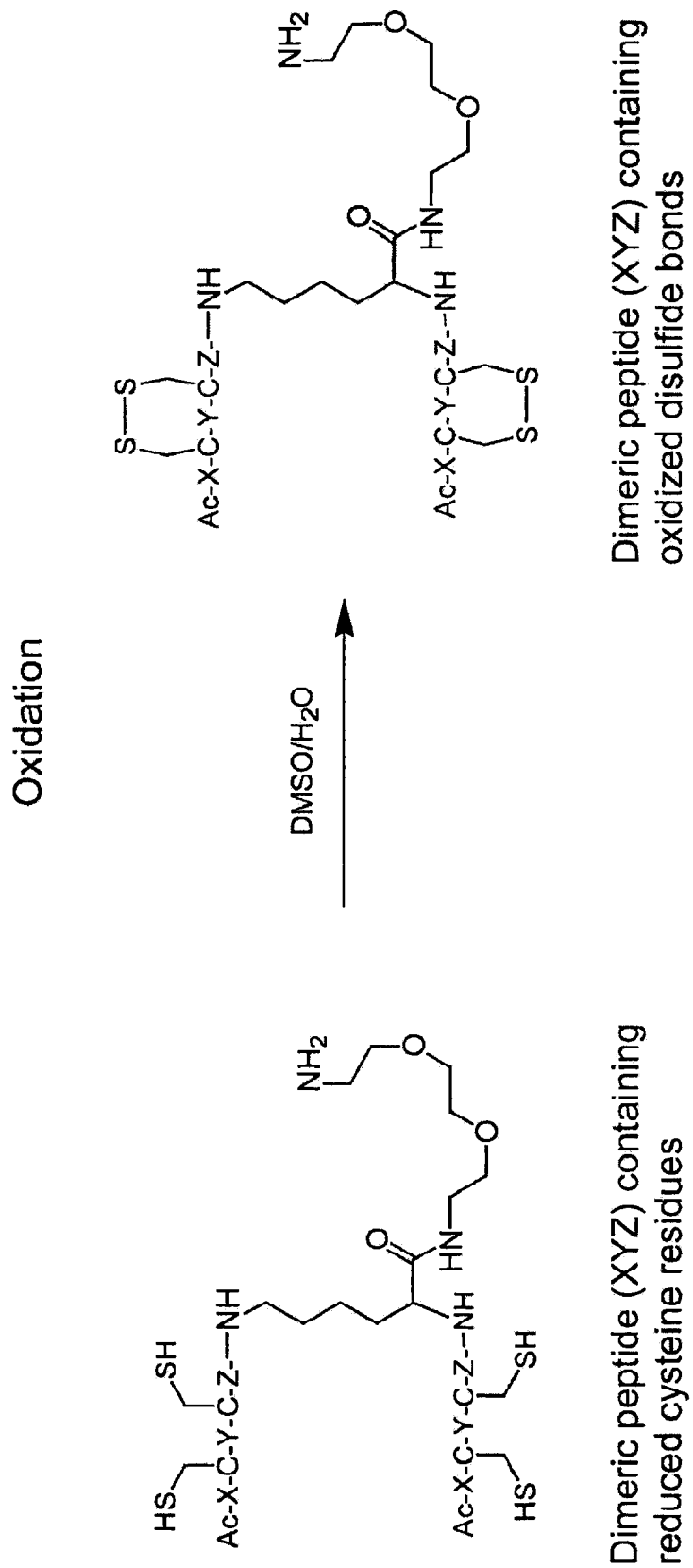

Dimeric peptide (attached to spacer) with reduced cysteine residues was oxidized to yield dimeric peptide with disulfide bonds as illustrated in FIG. 7F.
The dimeric peptide was dissolved in 20% DMSO/water (1 mg dry weight peptide/mL) and allowed to stand at room temperature for 36 hrs. The peptide was purified by loading the reaction mixture onto a C18 HPLC column (Waters Delta-Pak C18, 15 micron particle size, 300 angstrom pore size, 40 mm×200 mm length), followed by a linear ACN/water/0.01% TFA gradient from 5 to 95% ACN over 40 minutes.

Lypholization of the fractions containing the desired peptide yielded a fluffy white solid product.

Example 8

PEGylation of Peptide Dimer with Spacer, with mPEG-NPC

Figure 8A:
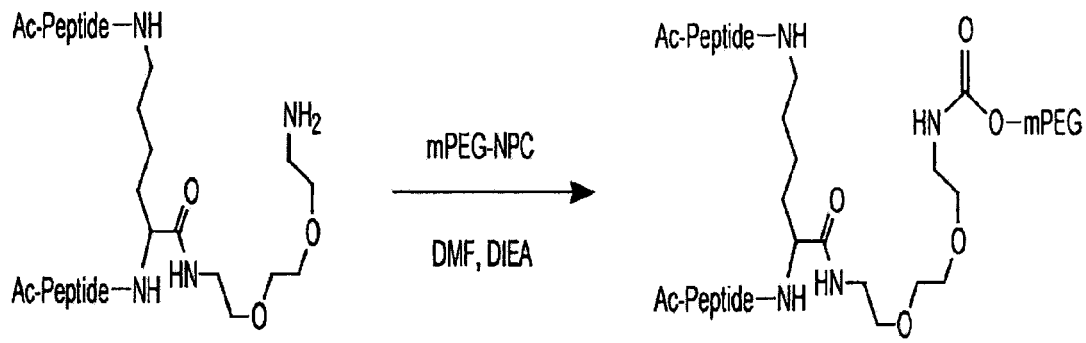
FIG. 8A shows a reaction scheme illustrating PEGylation of peptide dimer with spacer, with mPEG-NPC.
Figure 8B:
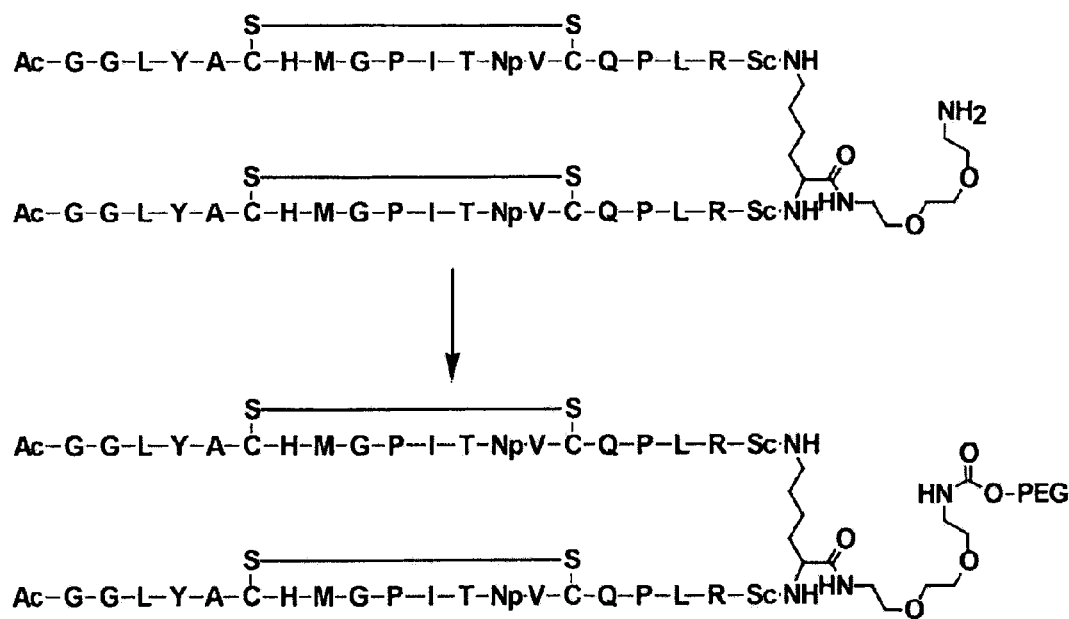
FIG. 8B illustrates the same reaction scheme for an exemplary peptide dimer, the monomer of which is SEQ ID NO:1. mPEG-NPC is these reactions has the structure illustrated in FIG. 8C.

FIG. 8A shows a reaction scheme illustrating PEGylation of peptide dimer with spacer, with mPEG-NPC. For example, FIG. 8B illustrates the reaction scheme for an exemplary peptide dimer, the monomer of which is SEQ ID NO:1.

Figure 8C:
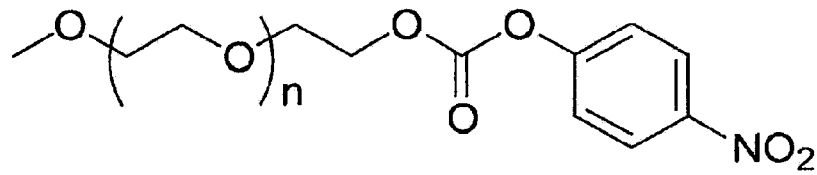

The dimeric peptide attached to the spacer, the monomer of which is SEQ ID NO:1, was mixed with an equal amount (mole basis) of activated PEG species (mPEG-NPC manufactured by NOF Corp., Japan, available through Nektar Therapeutics, U.S., (formerly "Shearwater Corp.")) in dry DMF to afford a clear solution. After 5 minutes, 4 eq. of DIEA was added to above solution. The mixture was stirred at ambient temperature for 14 hrs, followed by purification with C18 reverse phase HPLC. The structure of PEGylated peptide is confirmed by MALDI mass spectrometry.
mPEG-NPC has the structure illustrated in FIG. 8C.

Example 9

PEGylation of Peptide Dimer with Spacer, with mPEG-SPA

Figure 9A:
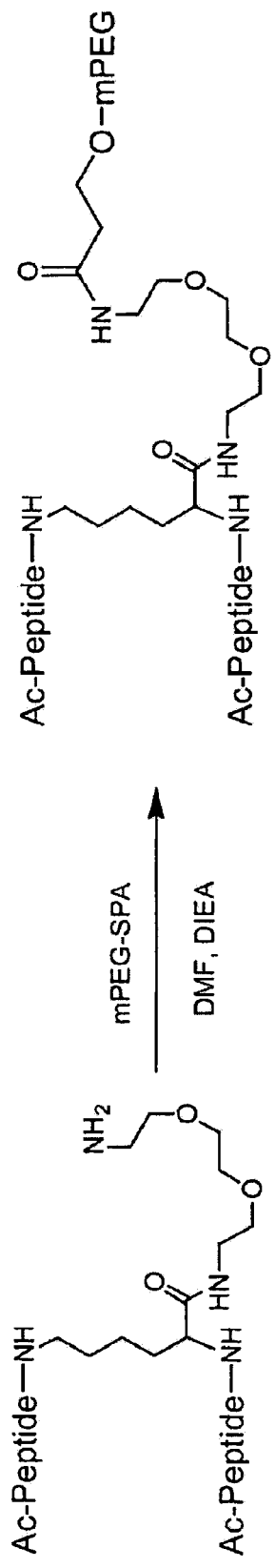
FIG. 9A shows a reaction scheme illustrating PEGylation of peptide dimer with spacer with mPEG-SPA, where the structure of mPEG-SPA is illustrated in FIG. 9B.
Figure 9B:
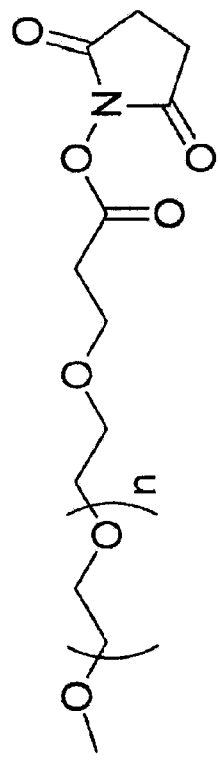

PEGylation of the peptide dimer with spacer can also by carried out with mPEG-SPA, as illustrated in the reaction scheme at FIG. 9A. mPEG-SPA has the structure illustrated in FIG. 9B.

Example 10

Ion Exchange Purification

Figure 10:
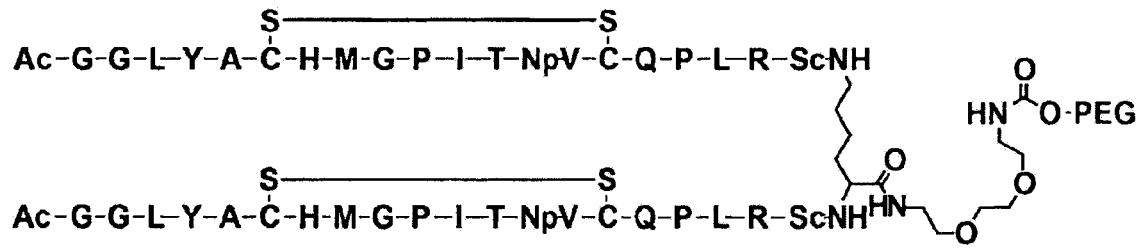
FIG. 10 illustrates the PEGylated peptide dimer obtained by the reaction scheme illustrated in FIG. 8B.

The sample obtained in Example 8 (FIG. 10) was used to identify ion exchange supports suitable for purifying peptide-Spacer-PEG conjugates.

The general procedure was as follows:
the ion exchange resin (2-3 g) was loaded into a 1 cm column, followed by conversion to the sodium form (0.2 N NaOH loaded onto column until elutant was at pH 14), and then to the hydrogen form (eluted with either 0.1 N HCl or 0.1 M HOAc until elutant matched load pH), followed by washing with 25% ACN/water until pH 6. Either the peptide prior to conjugation or the peptide-PEG conjugate was dissolved in 25% ACN/water (10 mg/mL) and the pH adjusted to below 3 with TFA, then loaded onto the column in separate experiments. After washing with 2-3 column volumes of 25% ACN/water and collecting 5 mL fractions, the peptide was released from the column by elution with 0.1 M $NH_4OAc$ in 25% ACN/water, again collecting 5 mL fractions. Analysis via HPLC revealed which fractions contained the desired peptide. Analysis with an Evaporative Light-Scattering Detector (ESLD) indicated that when the peptide was retained on the column and was eluted with the $NH_4OAc$ solution (generally between fractions 4 and 10), no non-conjugated PEG was observed as a contaminant. When the peptide eluted in the initial wash buffer (generally the first 2 fractions), no separation of desired PEG-conjugate and excess PEG was observed.

Ion exchange supports were chosen based their ability to separate the peptide-PEG conjugate from unreacted (or hydrolyzed) PEG as well as their ability to retain the starting dimeric peptides. Mono S HR 5/5 strong cation exchange pre-loaded column (Amersham Biosciences), SE53 Cellulose microgranular strong cation exchange support (Whatman), and SP Sepharose Fast Flow strong cation exchange support (Amersham Biosciences) were identified as suitable ion exchange supports.

Example 11

Synthesis of Trifunctional Molecules based on α-Amino Acids

Figure 11A:
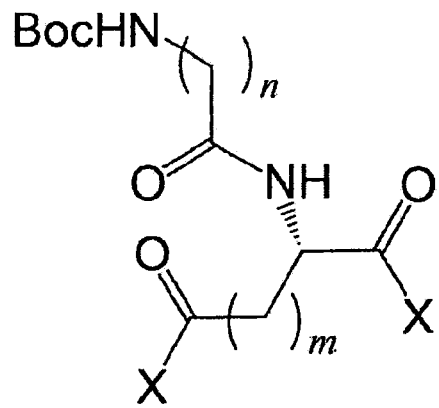
FIGS. 11A-11C illustrate synthesis of trifunctional molecules based on α-amino acids. The branched trifunctional molecules have the structure illustrated in FIG. 11A, where the substituent X may be selected from the chemical moieties illustrated in FIG. 11B.
Figure 11B:
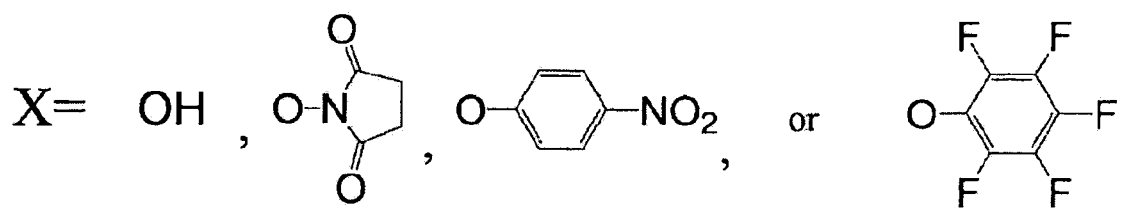
Figure 11C:
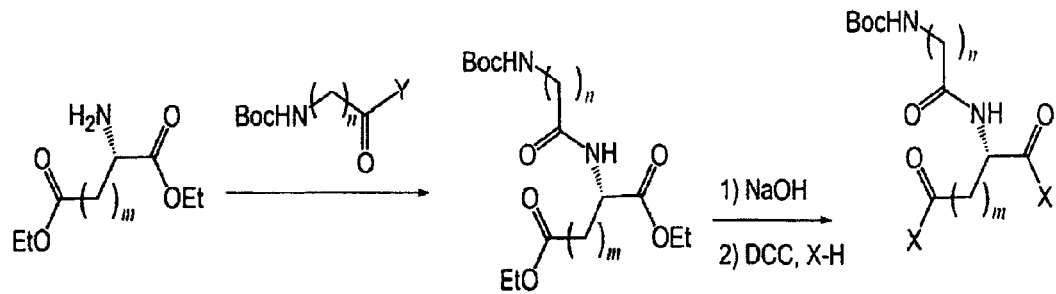

Branched trifunctional molecules having the structure shown in FIG. 11A,
wherein the X substituent may be selected from the chemical moieties illustrated in FIG. 11B,
were synthesized according to the reaction scheme shown in FIG. 11C.
Such trifunctional molecules can simultaneously act as a linker and a spacer.

Example 12

Synthesis of Trifunctional Molecules Based on Tertiary Amides

Figure 12A:
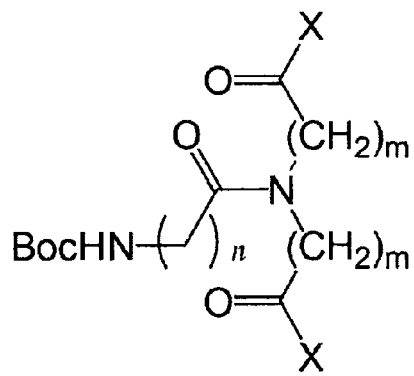
FIGS. 12A-12C illustrate synthesis of trifunctional molecules based on tertiary amides. The branched trifunctional molecules have the structure illustrated in FIG. 12A, where the substituent X may be selected from the chemical moieties illustrated in FIG. 12B.
Figure 12B:
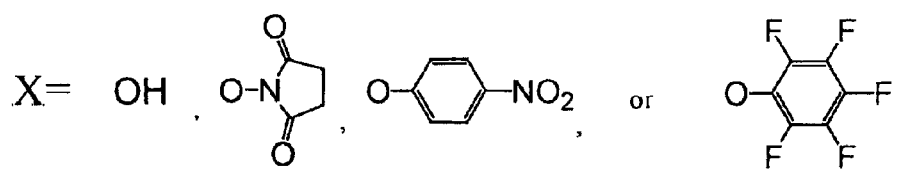
Figure 12C:
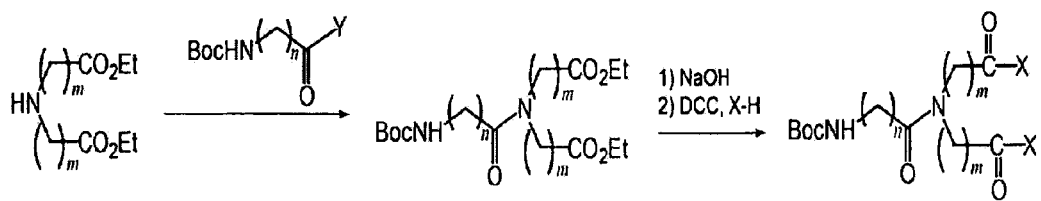

Branched trifunctional molecules having the structure illustrated in FIG. 12A, wherein the X substituent may be selected from the chemical moieties illustrated in FIG. 12B, were synthesized according to the reaction scheme shown in FIG. 12C.
Such trifunctional molecules can simultaneously act linker(s) and spacer.

Example 13

Synthesis of Homotrifunctional Molecules

Figure 13A:
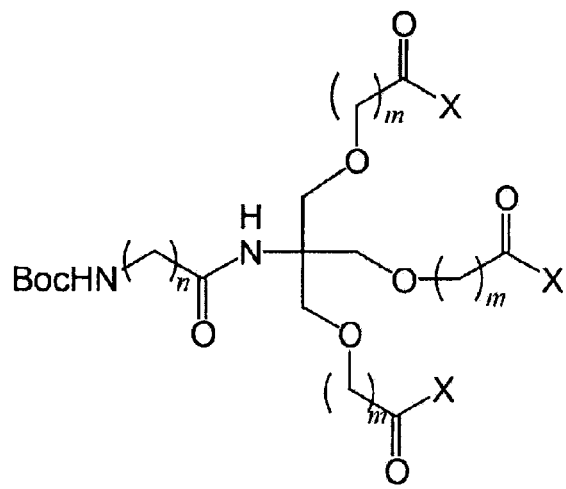
FIGS. 13A-13B illustrate synthesis of homotrifunctional molecules. The branched homotrifunctional molecules have the structure illustrated in FIG. 13A, where the substituent X may be selected from the chemical moieties illustrated in that figure.
Figure 13A:
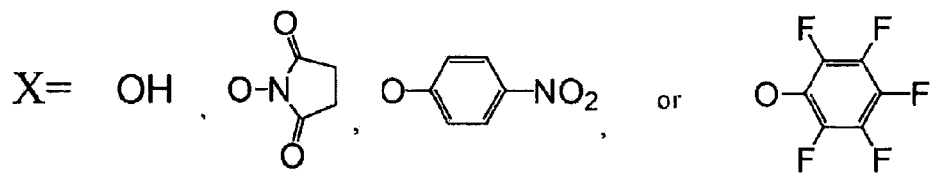
Figure 13B:
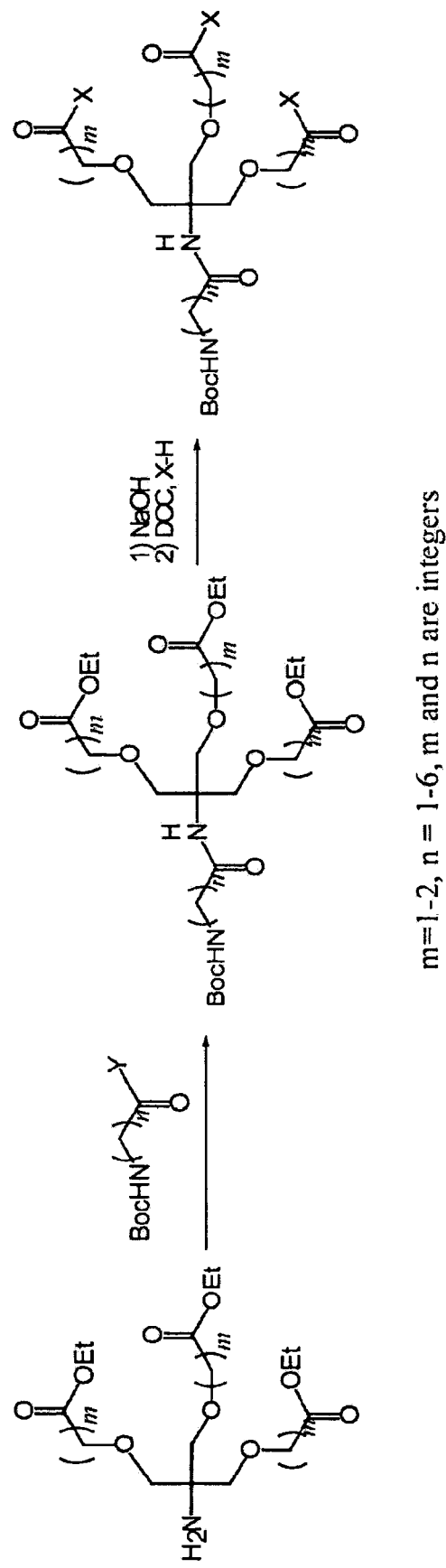

Branched homotrifunctional molecules having the structure illustrated in FIG. 13A, wherein the X substituent may be selected from the chemical moieties illustrated in that figure, were synthesized according to the reaction scheme shown in FIG. 13B.
Such homotrifunctional molecules can simultaneously act linker(s) and spacer.

Example 14

C-Terminus Dimerization and PEGylation Using A Trifunctional Molecule

Figure 14A:
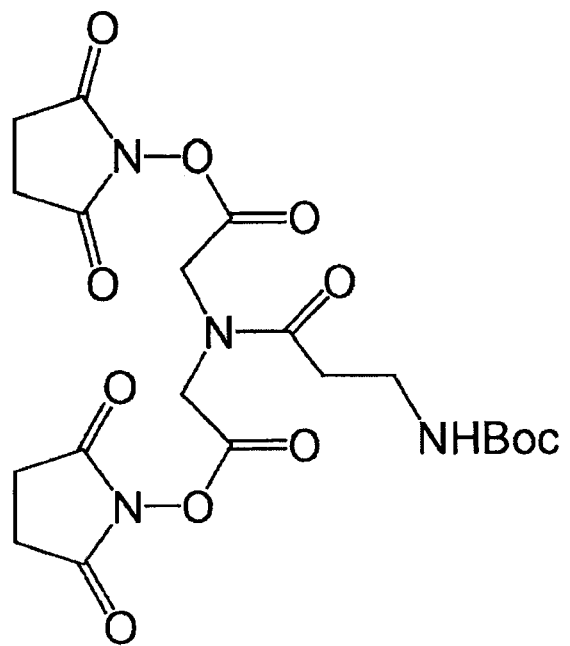
FIGS. 14A-14B illustrate C-terminus dimerization and PEGylation using a trifunctional linker molecule having the structure illustrated in FIG. 14A.

Branched homotrifunctional molecules having the structure illustrated in FIG. 14A was made according to Example 12.

Figure 14B:
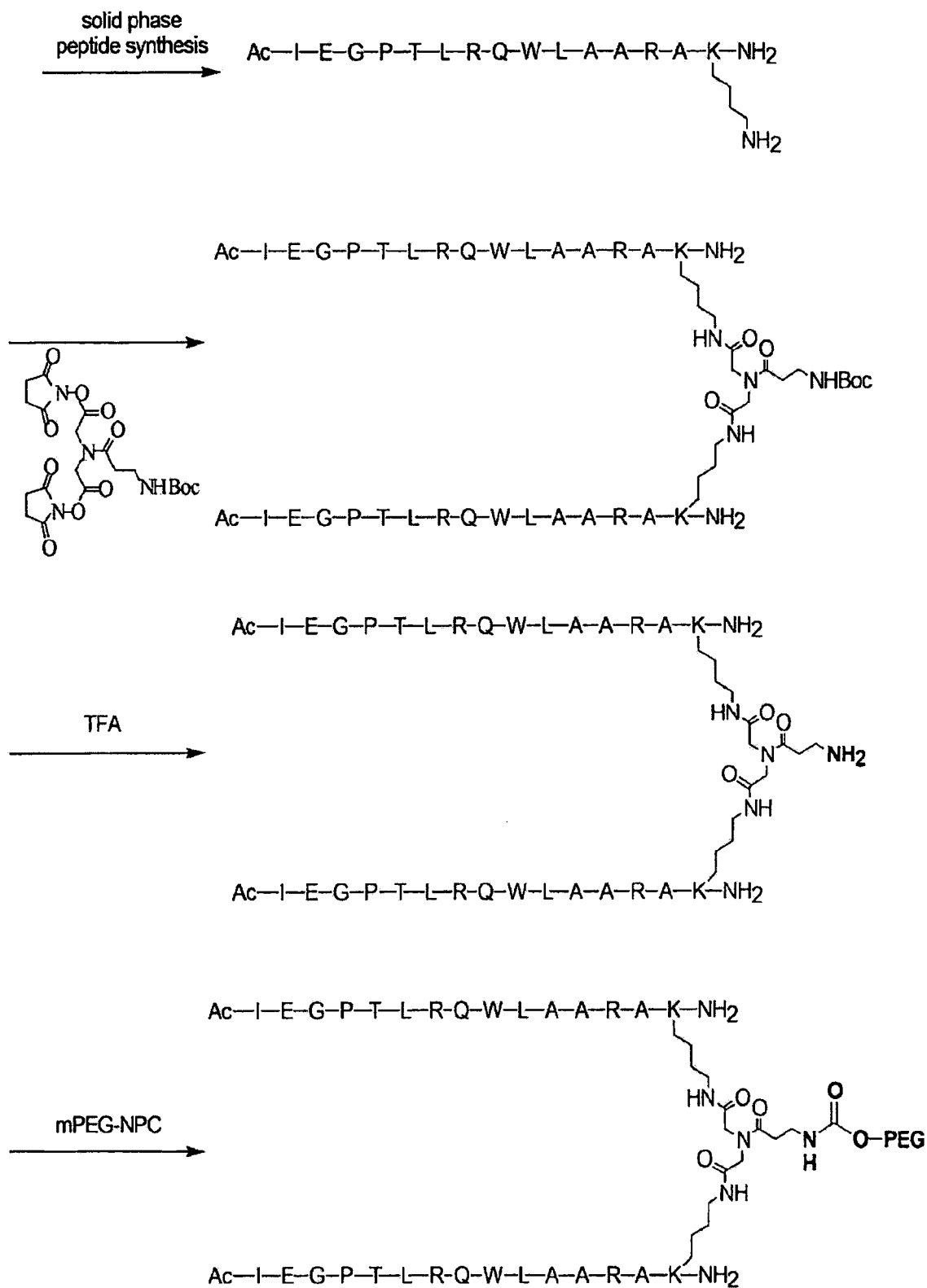

This trifunctional molecule was used in C-terminus dimerization and PEGylation according to the reaction scheme illustrated in FIG. 14B (utilizing SEQ ID NO:2).

Example 15

N-Terminus Dimerization and PEGylation Using A Trifunctional Molecule

Figure 15A:
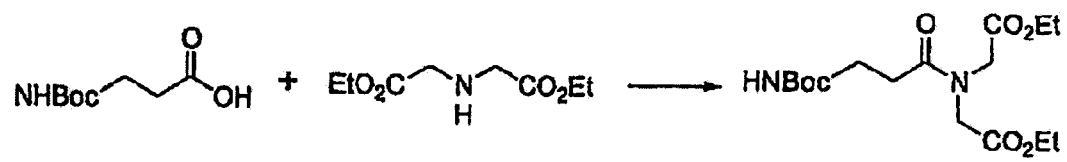
FIGS. 15A-15D illustrate reaction schemes for N-terminal dimerization and PEGylation using a trifunctional molecule.
Figure 15B:
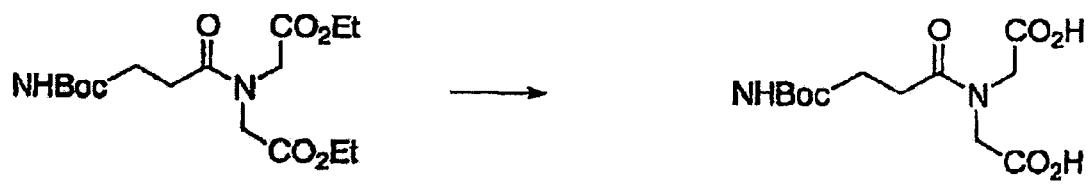
Figure 15C:
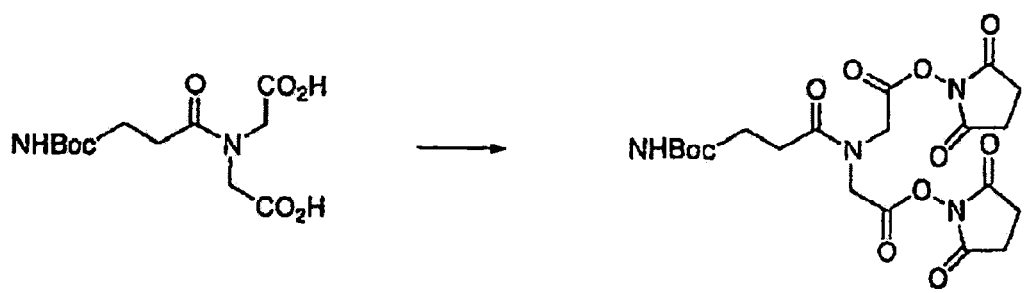

The trifunctional molecule was made according to the reaction schemes illustrated in FIGS. 15A-15C.

To a solution of Boc-βAla-OH (10.0 g, 52.8 mmol) (Boc=tert-butoxycarbonyl) and diethyl iminodiacetate (10.0 g, 52.8 mmol) in 200 mL of DCM at 0° C. was added DCC (10.5 g, 50.9 mmol) over 5 min. A white precipitate formed within 2 min. The reaction mixture was allowed to warm to room temperature and was stirred for 24 h. The urea was filtered off with a sintered filter (medium porosity) and the solvent removed under reduced pressure. The residue was taken up in 500 mL of EtOAc (EtOAc=ethyl acetate), filtered as above, and transferred to a separatory funnel. The organic phase was washed (sat. NaHCO$_3$, brine, 1 N HCl, brine), dried (MgSO$_4$), filtered, and dried to yield a colorless oil. The oil solidified to yield a white crystalline solid within 10 min.

The crude diester was taken up in 75 mL of THF (THF=tetrahydrofurane) and 75 mL of MeOH (MeOH=methanol) and 50 mL of water was added. To this solution was added a solution of KOH (KOH=potassium hydroxide) (8.6 g, 153 mmol) in 25 mL of water. The reaction mixture turned light yellow in color. After stirring for 12 h (pH was still ~12), the organic solvent was removed on a rotary evaporator and the resultant slurry partitioned between Et$_2$O (Et$_2$O=Diethyl ether) and sat. NaHCO$_3$. The combined aq. phase was acidified to pH 1, saturated with NaCl, and extracted with EtOAc. The EtOAc phase was washed (brine), dried (MgSO$_4$), and concentrated to yield 13.97 g of product as a white solid (90.2% for 2 steps).

Notes: the yield dropped to 73% when the DCC reaction was performed in ACN. When using DIC, the urea byproduct could not be removed from the desired product without chromatography; the DCC urea can be quantitatively removed without chromatography. The reaction also works well with water-soluble carbodiimide.

To a solution of diacid (1.00 g, 3.29 mmol) and hydroxysuccinimide (0.945 g, 8.21 mmol) in 50 mL of ACN was added DCC (1.36 g, 6.59 mmol) over 5 min. A white ppt formed immediately. The reaction mixture was stirred 22 h and was filtered to remove the DCC urea. The solvent was removed under reduced pressure and the residue taken up in EtOAc (250 mL) and transferred to a separatory funnel. The organic phase was washed (sat. NaHCO$_3$, brine, 1 N HCl, brine), dried (MgSO$_4$), and concentrated to afford a white solid. The solid was taken up in 75 mL of ACN, filtered, and concentrated to yield 1.28 g of product as a white solid (78.2% yield).

Notes: the yields dropped to 31% in THF, 68% in DMF (with DIC instead of DCC), and 57% in DCM/DMF. The starting diacid is soluble in ACN, so if there is any material which has not dissolved before the DCC is added, it may be filtered off and discarded.

Figure 15D:
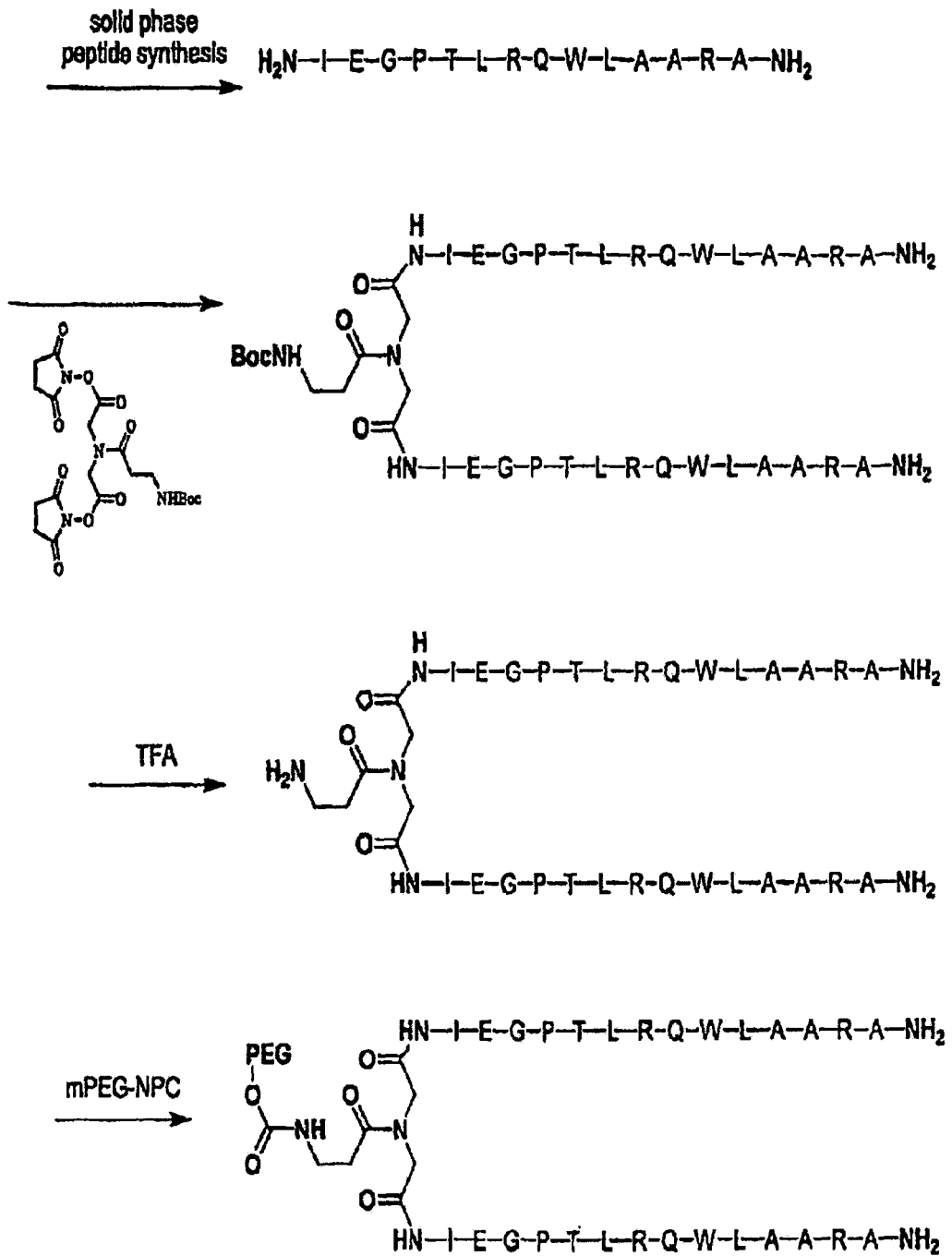

This trifunctional molecule was used in N-terminus dimerization and PEGylation according to the reaction scheme illustrated in FIG. 15D (utilizing SEQ ID NO:3).

Examples 16

Synthesis of mPEG$_2$-Lysinol-NPC

Commercially available lysinol is treated with an excess of mPEG$_2$ resulting in the formation of mPEG$_2$-Lysinol. Thereafter, mPEG$_2$-Lysinol is treated with excessive NPC forming PEG$_2$-Lysinol-NPC Example 17

PEGylation Using A Trifunctional Molecule (PEG Moiety Comprises Two Linear PEG Chains)

Figure 16A:
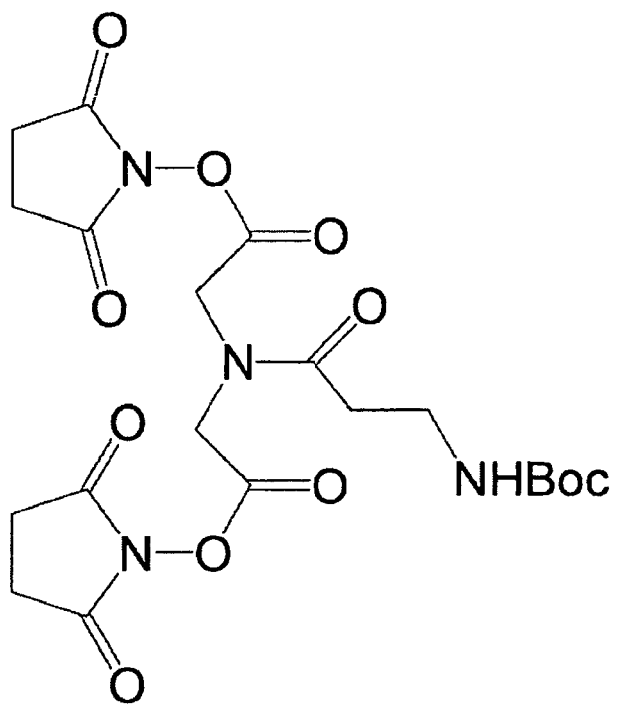
FIGS. 16A-16D illustrate reaction schemes for PEGylation using a trifunctional linker with PEG moiety comprising two linear PEG chains.

A trifunctional molecular having the structure illustrated in FIG. 16A was made according to Example 15.

Figure 16B:
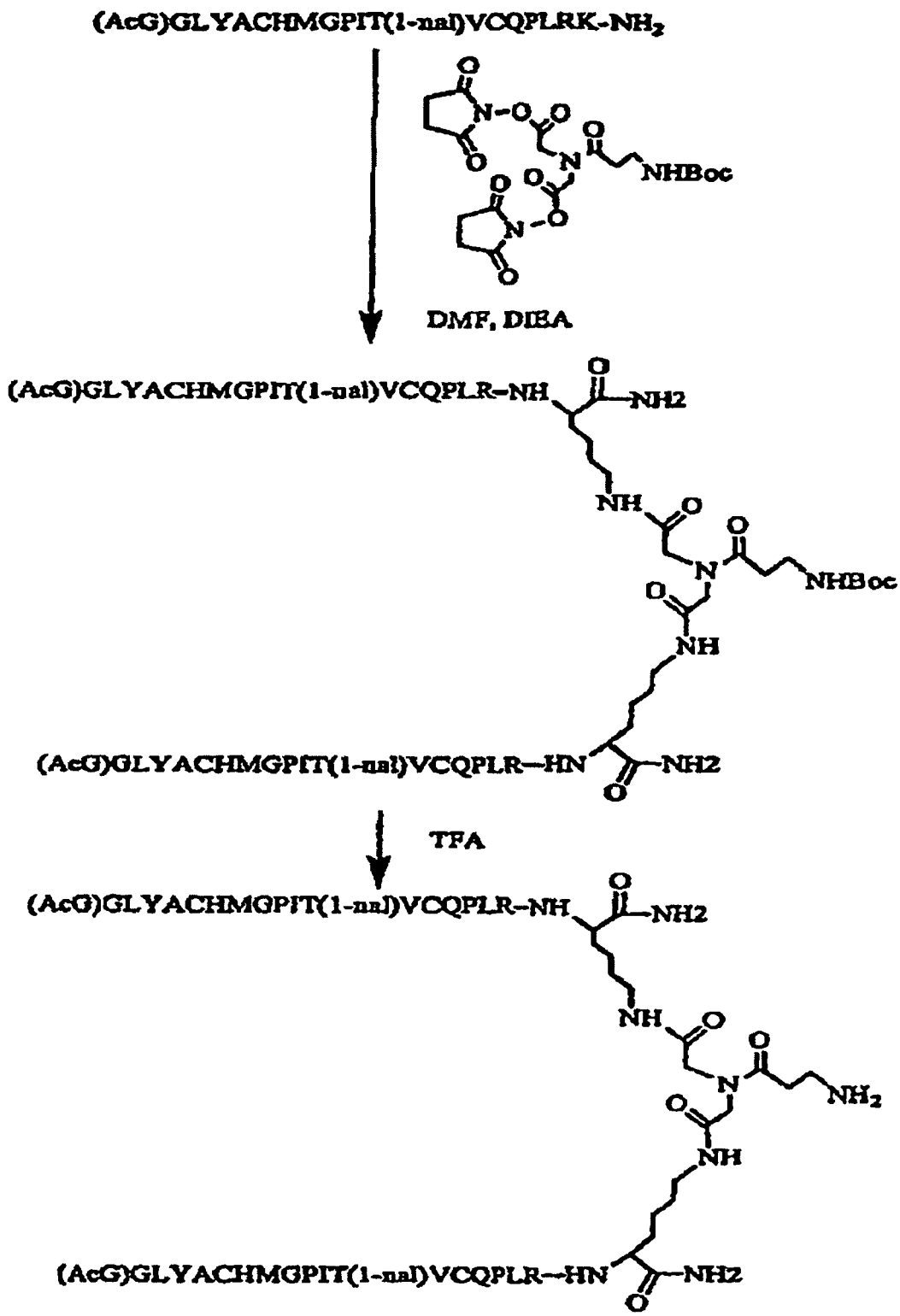

Coupling of the Trifunctional Linker to the Peptide Monomers:

For coupling to the linker, 2 eq peptide is mixed with 1 eq of trifunctional linker in dry DMF to give a clear solution, and 5 eq of DIEA is added after 2 minutes. The mixture is stirred at ambient temperature for 14 h. The solvent is removed under reduced pressure and the crude product is dissolved in 80% TFA in DCM for 30 min to remove the Boc group, followed by purification with C18 reverse phase HPLC. The structure of the dimer is confirmed by electrospray mass spectrometry. This coupling reaction attaches the linker to the nitrogen atom of the ε-amino group of the lysine residue of each monomer (SEQ ID NO:4 in the reaction scheme illustrated in FIG. 16B).

Figure 16C:
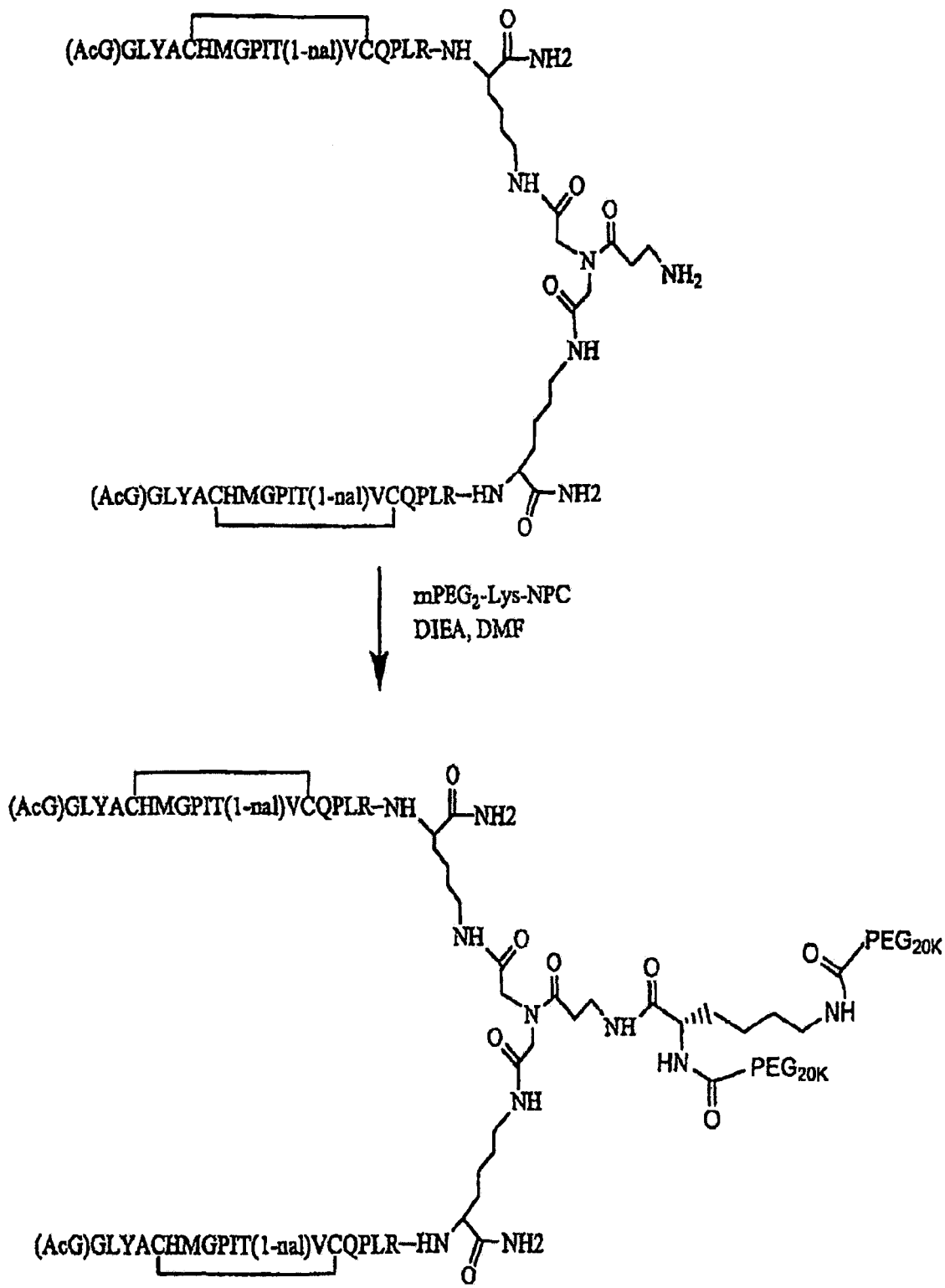

PEGylation of the Peptide Dimer:
PEGylation Via a Carbamate Bond (FIG. 16c):

The peptide dimer and the PEG species (mPEG$_2$-Lysinol-NPC) are mixed in a 1:2 molar ratio in dry DMF to afford a clear solution. After 5 minutes 4 eq of DIEA is added to above solution. The mixture is stirred at ambient temperature 14 h, followed by purification with C18 reverse phase HPLC. The structure of PEGylated peptide is confirmed by MALDI mass. The purified peptide was also subjected to purification via cation ion exchange chromatography.

Figure 16D:
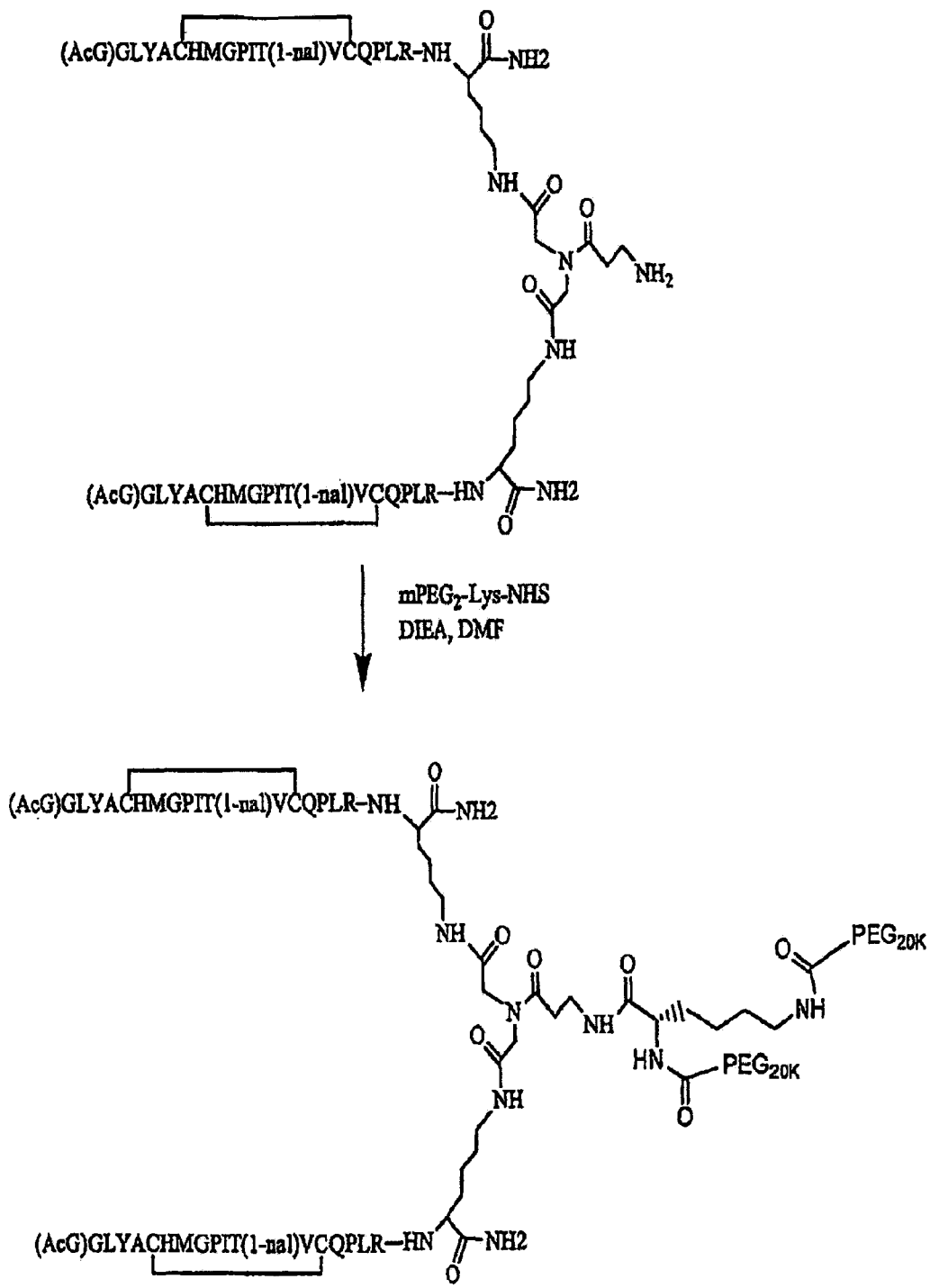

PEGylation Via an Amide Bond (FIG. 16D):

The peptide dimer and PEG species [mPEG$_2$-Lys-NHS] are mixed in a 1:2 molar ratio in dry DMF to afford a clear solution. After 5 minutes 10 eq of DIEA is added to above solution. mPEG$_2$-Lys-NHS may be obtained commercially, for example, from the Molecular Engineering catalog (2003) of Nektar Therapeutics (490 Discovery Drive, Huntsville, Ala. 35806), item no. 2Z3X0T01. The mixture is stirred at ambient temperature 2 h, followed by purification with C18 reverse phase HPLC. The structure of PEGylated peptide was confirmed by MALDI mass. The purified peptide was also subjected to purification via cation ion exchange chromatography as outlined below.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Numerous references, including patents, patent applications, protocols and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entirety and to the same extent as if each reference was individually incorporated by reference.

What is claimed is:

1. A compound comprising a peptide moiety, a spacer moiety, and a water-soluble polymer moiety wherein:
the peptide moiety comprises at least one peptide monomer;
the spacer moiety is between the peptide moiety and the water-soluble polymer moiety, and has the structure:

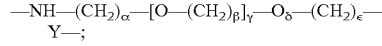

α is an integer, 1≤α≤6;
β is an integer, 1≤β≤6;
ε is an integer, 1≤ε≤6;

δ is 0 or 1;
γ is an integer, 0≤γ≤10; and
Y is either NH or CO.

2. The compound of claim 1, wherein the peptide moiety is a peptide monomer comprising a single peptide.

3. The compound of claim 1, wherein the peptide moiety comprises two peptide monomers linked by a linker moiety.

4. The compound of claim 1, wherein the peptide moiety comprises one or more peptides which bind to thrombopoietin-receptors.

5. A pharmaceutical composition comprising
   (a) a compound comprising a peptide moiety, a spacer moiety and a water-soluble polymer moiety; and
   (b) one or more pharmaceutically acceptable diluents, preservatives, solubilizers, emulsifiers, adjuvants or carriers
   wherein:
      the peptide moiety comprises at least one peptide monomer,
      the spacer moiety is between the peptide moiety and the water-soluble polymer moiety and has the structure:

α is an integer, 1≤α≤6;
β is an integer, 1≤β≤6;
ε is an integer, 1≤ε≤6;
δ is 0 or 1;
γ is an integer, 0≤γ≤10; and
Y is either NH or CO.

6. The composition of claim 5, wherein the peptide moiety is peptide monomer comprising a single peptide.

7. The composition of claim 5, wherein the peptide moiety comprises two peptide monomers linked by a linker moiety.

8. The composition of claim 5, wherein the peptide moiety comprises one or more peptides which bind to thrombopoietin-receptors.

9. The compound according to claim 3, wherein the linker moiety has the structure

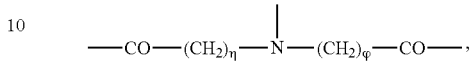

N of the linker moiety is covalently attached to Y of the spacer moiety,
Y of the spacer moiety is CO, and
η and φ are integers whose values are independently selected.

10. The composition according to claim 7, wherein the linker moiety has the structure

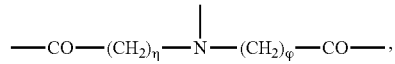

N of the linker moiety is covalently attached to Y of the spacer moiety,
Y of the spacer moiety is CO, and
η and φ are integers whose values are independently selected.

* * * * *